United States Patent
Díaz Fernández et al.

(10) Patent No.: US 9,278,974 B2
(45) Date of Patent: Mar. 8, 2016

(54) SUBSTITUTED PYRAZOLO[3,4-D]PYRIMIDINE COMPOUNDS, THEIR PREPARATION AND USE AS SIGMA RECEPTORS LIGANDS

(71) Applicant: LABORATORIOS DEL DR. ESTEVE S.A., Barcelona (ES)

(72) Inventors: José Luis Díaz Fernández, Manresa (ES); Carme Almansa, Barcelona (ES); Jordi Corbera Arjona, Terrassa (ES)

(73) Assignee: LABORATORIOS DEL DR. ESTEVE S.A., Barcelona (ES)

( * ) Notice: Subject to any disclaimer, the term of this patent is extended or adjusted under 35 U.S.C. 154(b) by 0 days.

(21) Appl. No.: 14/442,816

(22) PCT Filed: Nov. 14, 2013

(86) PCT No.: PCT/EP2013/073801
§ 371 (c)(1),
(2) Date: May 14, 2015

(87) PCT Pub. No.: WO2014/076170
PCT Pub. Date: May 22, 2014

(65) Prior Publication Data
US 2015/0315192 A1    Nov. 5, 2015

(30) Foreign Application Priority Data
Nov. 14, 2012 (EP) .................................... 12382448

(51) Int. Cl.
C07D 293/06 (2006.01)
C07H 21/00 (2006.01)
C07D 487/04 (2006.01)

(52) U.S. Cl.
CPC .................................. C07D 487/04 (2013.01)

(58) Field of Classification Search
CPC .............................. C07D 293/06; C07H 21/00
See application file for complete search history.

(56) References Cited

FOREIGN PATENT DOCUMENTS

| | | | |
|---|---|---|---|
| EP | 1634873 A1 | 3/2006 | |
| EP | 1847542 A1 | 10/2007 | |
| WO | 2006/021463 A1 | 3/2006 | |
| WO | 2009/071657 A1 | 3/2006 | |
| WO | 2007/098961 A | 9/2007 | |
| WO | 2008/049105 A2 | 4/2008 | |
| WO | 2010/056320 A2 | 5/2010 | |

OTHER PUBLICATIONS

Hayashi et al., caplus an 1978:615358 (1978).*
Taylor et al., caplus an 1960:17039 (1960).*
Gillespie et al. (2002) caplus an 2002:539533.*
Teruo et al., 2011, http://www.ncbi.nlm.nih.gov/pmc/articles/PMC3076924/.*
Maurice et al., Pharmacopsychiatry, 2004, 37, S198-S207.*
Nguyen et al., Journal of Pharmacological Sciences, 2015, 127, 17-29.*
Romero et al., 2012, http://www.ncbi.nlm.nih.gov/pubmed/22404321.*
Bowen, et al., Pharmaceutica Acta Helvetiae, vol. 74, p. 211-218, 2000.
Dehaven-Hudkins, et al., European Journal of Pharmacology—Molecular Pharmacology Section, vol. 227, p. 371-378, 1992.
Diaz, et al., Central Nervous System Agents in Medicinal Chemistry, vol. 9, p. 172-183, 2009.
European Search Report for EP12382448 of Jan. 16, 2013.
Hanner, et al., Proc. Natl. Acad. Sci. USA, vol. 93, p. 8072-8077, Jul. 1996.
International Search Report for PCT/EP2013/073801 of Dec. 2, 2013.
Kaiser, Neurotransmissions, vol. 7, No. 1, p. 1-5, 1991.
Merskey, et al., Classification of Chronic Pain Second Edition, p. 210-213, 2002.
Quirion, Tips, vol. 13, p. 85-86, Mar. 1992.
Ronsisvalle, et al., Pure Appl Chem, vol. 73, No. 9, p. 1499-1509, 2001.
Snyder, et al., Journal of Neuropsychiatry, vol. 1, No. 1, p. 7-15, Winter 1989.
Walker, et al., Pharmacological Review., vol. 42, No. 4, p. 355-402.

* cited by examiner

Primary Examiner — Sun Jae Yoo
(74) Attorney, Agent, or Firm — Hueschen and Sage

(57) ABSTRACT

The present invention relates to new substituted pyrazolo[3,4-d]pyrimidine compounds, having a great affinity for sigma receptors, especially sigma-1 receptor, as well as to the process for the preparation thereof, to compositions comprising them, and to their use as medicaments.

14 Claims, No Drawings

SUBSTITUTED PYRAZOLO[3,4-D]PYRIMIDINE COMPOUNDS, THEIR PREPARATION AND USE AS SIGMA RECEPTORS LIGANDS

FIELD OF THE INVENTION

The present invention relates to new substituted pyrazolo [3,4-d]pyrimidine compounds, having a great affinity for sigma receptors, especially sigma-1 receptor, as well as to the process for the preparation thereof, to compositions comprising them, and to their use as medicaments.

BACKGROUND OF THE INVENTION

The search for new therapeutic agents has been greatly aided in recent years by better understanding of the structure of proteins and other biomolecules associated with target diseases. One important class of these proteins are the sigma (σ) receptors, cell surface receptors of the central nervous system (CNS) which may be related to the dysphoric, hallucinogenic and cardiac stimulant effects of opioids. From studies of the biology and function of sigma receptors, evidence has been presented that sigma receptor ligands may be useful in the treatment of psychosis and movement disorders such as dystonia and tardive dyskinesia, and motor disturbances associated with Huntington's chorea or Tourette's syndrome and in Parkinson's disease (Walker, J. M. et al, Pharmacological Reviews, 1990, 42, 355). It has been reported that the known sigma receptor ligand rimcazole clinically shows effects in the treatment of psychosis (Snyder, S. H., Largent, B. L. J. Neuropsychiatry 1989, 1, 7). The sigma binding sites have preferential affinity for the dextrorotatory isomers of certain opiate benzomorphans, such as SKF 10047, (+)-cyclazocine, and (+)-pentazocine and also for some narcoleptics such as haloperidol.

"The sigma receptor/s" as used in this application is/are well known and defined using the following citation: This binding site represents a typical protein different from opioid, NMDA, dopaminergic, and other known neurotransmitter or hormone receptor families (G. Ronsisvalle et al. Pure Appl. Chem. 73, 1499-1509 (2001)).

The sigma receptor has at least two subtypes, which may be discriminated by stereoselective isomers of these pharmaco-active drugs. SKF 10047 has nanomolar affinity for the sigma 1 (σ-1) site, and has micromolar affinity for the sigma 2 (σ-2) site. Haloperidol has similar affinities for both subtypes.

The Sigma-1 receptor is a non-opiaceous type receptor expressed in numerous adult mammal tissues (e.g. central nervous system, ovary, testicle, placenta, adrenal gland, spleen, liver, kidney, gastrointestinal tract) as well as in embryo development from its earliest stages, and is apparently involved in a large number of physiological functions. Its high affinity for various pharmaceuticals has been described, such as for SKF-10047, (+)-pentazocine, haloperidol and rimcazole, among others, known ligands with analgesic, anxiolytic, antidepressive, antiamnesic, antipsychotic and neuroprotective activity. Sigma-1 receptor is of great interest in pharmacology in view of its possible physiological role in processes related to analgesia, anxiety, addiction, amnesia, depression, schizophrenia, stress, neuroprotection and psychosis [Kaiser et al (1991) Neurotransmissions 7 (1): 1-5], [Walker, J. M. et al, Pharmacological Reviews, 1990, 42, 355] and [Bowen W. D. (2000) Pharmaceutica Acta Helvetiae 74: 211-218].

The Sigma-2 receptor is also expressed in numerous adult mammal tissues (e.g. nervous system, immune system, endocrine system, liver, kidney). Sigma-2 receptors can be components in a new apoptosis route that may play an important role in regulating cell proliferation or in cell development. This route seems to consist of Sigma-2 receptors joined to intracellular membranes, located in organelles storing calcium, such as the endoplasmic reticulum and mitochondria, which also have the ability to release calcium from these organelles. The calcium signals can be used in the signaling route for normal cells and/or in induction of apoptosis.

Agonists of Sigma-2 receptors induce changes in cell morphology, apoptosis in several types of cell lines and regulate the expression of p-glycoprotein mRNA, so that they are potentially useful as antineoplasic agents for treatment of cancer. In fact, Sigma-2 receptor agonists have been observed to induce apoptosis in mammary tumour cell lines resistant to common antineoplasic agents that damage DNA. In addition, agonists of Sigma-2 receptors enhance the cytotoxic effects of these antineoplasic agents at concentrations in which the agonist is not cytotoxic. Thus, agonists of Sigma-2 receptors can be used as antineoplasic agents at doses inducing apoptosis or at sub-toxic doses in combination with other antineoplasic agents to revert the resistance to the drug, thereby allowing using lower doses of the antineoplasic agent and considerably reducing its adverse effects.

Antagonists of Sigma-2 receptors can prevent the irreversible motor side effects caused by typical neuroleptic agents. In fact, it has been found that antagonists of Sigma-2 receptors can be useful as agents for improving the weakening effects of delayed dyskinesia appearing in patients due to chronic treatment of psychosis with typical antipsychotic drugs, such as haloperidol. Sigma-2 receptors also seem to play a role in certain degenerative disorders in which blocking these receptors could be useful.

Endogenous sigma ligands are not known, although progesterone has been suggested to be one of them. Possible sigma-site-mediated drug effects include modulation of glutamate receptor function, neurotransmitter response, neuroprotection, behavior, and cognition (Quirion, R. et al. Trends Pharmacol. Sci., 1992, 13:85-86). Most studies have implied that sigma binding sites (receptors) are plasmalemmal elements of the signal transduction cascade. Drugs reported to be selective sigma ligands have been evaluated as antipsychotics (Hanner, M. et al. Proc. Natl. Acad. Sci., 1996, 93:8072-8077). The existence of sigma receptors in the CNS, immune and endocrine systems have suggested a likelihood that it may serve as link between the three systems.

In view of the potential therapeutic applications of agonists or antagonists of the sigma receptor, a great effort has been directed to find selective ligands. Different sigma receptor ligands have been reported.

For instance, the international patent application WO 2007/098961 describes 4,5,6,7 tetrahydrobenzo[b]thiophene derivatives having pharmacological activity towards the sigma receptor.

Spiro[benzopyran] or spiro[benzofuran] derivatives were also disclosed in EP 1 847 542 as well as pyrazole derivatives (EP 1 634 873) with pharmacological activity on sigma receptors.

WO 2009/071657 also reports tricyclic triazolic compounds having good activity towards sigma receptors.

WO 2008049105 discloses some pyrazolo[3,4-d]pyrimidine compounds but they are inhibitors of Heat Shock Protein 90 (HSP90) and useful to treat disorders mediated by HSP90.

Nevertheless, there is still a need to find compounds having pharmacological activity towards the sigma receptor, being both effective and selective, and having good "drugability"

properties, i.e. good pharmaceutical properties related to administration, distribution, metabolism and excretion.

Surprisingly, the authors of the present invention have observed that new pyrazolo[3,4-d]pyrimidine compounds with general formula (I) show an affinity for Sigma receptor ranging from good to excellent. These compounds are therefore particularly suitable as pharmacologically active agents in medicaments for the prophylaxis and/or treatment of disorders or diseases related to Sigma receptors

SUMMARY OF THE INVENTION

The present invention discloses novel compounds with significant affinity to sigma receptors which might be used for the treatment of sigma related disorders or diseases.

Specifically, it is an object of the present invention the novel substituted pyrazolo[3,4-d]pyrimidine compounds of general formula (I):

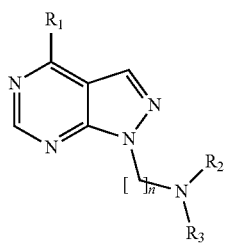

(I)

Another object of the invention is the process for preparation of compounds of general formula (I).

Another object of the invention refers to the use of such compounds of general formula (I) for the treatment or prophylaxis of sigma receptor mediated diseases or conditions, especially sigma-1 mediated diseases or conditions. Within the group of diseases or conditions mediated by sigma receptor for which the compounds of the invention are effective diarrhea, lipoprotein disorders, hyperlipidemia, hypertriglyceridemia, hypercholesterolemia, obesity, migraine, arthritis, hypertension, arrhythmia, ulcer, glaucoma, learning, memory and attention deficits, cognition disorders, neurodegenerative diseases, demyelinating diseases, addiction to drugs and chemical substances including cocaine, amphetamine, ethanol and nicotine; tardive dyskinesia, ischemic stroke, epilepsy, stroke, stress, cancer, psychotic conditions, in particular depression, anxiety or schizophrenia; inflammation or autoimmune diseases, may be cited. Compounds of the invention are very good and are especially effective for the treatment and prophylaxis of pain, especially neuropathic pain, inflammatory pain or other pain conditions involving allodynia and/or hyperalgesia.

It is also an object of the invention pharmaceutical compositions comprising one or more compounds of general formula (I) with at least one pharmaceutically acceptable excipient. The pharmaceutical compositions in accordance with the invention can be adapted in order to be administered by any route of administration, be it orally or parenterally, such as pulmonarily, nasally, rectally and/or intravenously. Therefore, the formulation in accordance with the invention may be adapted for topical or systemic application, particularly for dermal, subcutaneous, intramuscular, intra-articular, intraperitoneal, pulmonary, buccal, sublingual, nasal, percutaneous, vaginal, oral or parenteral application.

DETAILED DESCRIPTION OF THE INVENTION

The invention first relates to a compound of general formula (I):

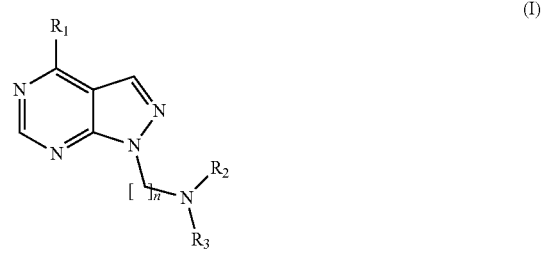

(I)

wherein
n is selected from 1, 2, 3 or 4;
$R_1$ represents a carbon-linked substituted or unsubstituted aryl or heteroaryl radical;
$R_2$ and $R_3$ independently represent a hydrogen atom;
a branched or unbranched, saturated or unsaturated, optionally at least mono-substituted, aliphatic radical $C_{1-10}$;
a substituted or unsubstituted cycloalkyl radical $C_{3-9}$; a branched or unbranched cycloalkyl-alkyl radical $C_{1-10}$ group in which either the alkyl group and/or the cycloalkyl group is optionally at least mono-substituted;
a substituted or unsubstituted cycloalkyl $C_{3-9}$ or cycloalkylalkyl $C_{1-10}$ group in which the cycloalkyl group is condensed with another substituted or unsubstituted mono- or polycyclic ring system;
a substituted or unsubstituted aryl radical; a substituted or unsubstituted, branched or unbranched arylalkyl radical $C_{1-10}$;
a substituted or unsubstituted heteroaryl radical; a substituted or unsubstituted, branched or unbranched heteroarylalkyl radical $C_{1-10}$; a substituted or unsubstituted non-aromatic heterocyclyl radical $C_{3-9}$; a substituted or unsubstituted, branched or unbranched heterocyclylalkyl radical $C_{3-9}$;
a substituted or unsubstituted heterocyclyl $C_{3-9}$ or heterocyclyl-alkyl radical $C_{1-10}$ group in which the heterocyclyl group is condensed with another substituted or unsubstituted mono- or polycyclic ring system;
or $R_2$ and $R_3$ together with the bridging nitrogen form a substituted or unsubstituted heterocycloalkyl radical $C_{3-9}$; or a substituted or unsubstituted heteroaryl radical $C_{3-9}$;
or a pharmaceutically acceptable salt, isomer, prodrug or solvate thereof.

"Halogen" or "halo" as referred in the present invention represent fluorine, chlorine, bromine or iodine.

Aliphatic group/radicals $C_{1-10}$, as referred to in the present invention, are optionally mono- or polysubstituted and may be branched or unbranched, saturated or unsaturated. Unsaturated aliphatic groups, as defined in the present invention, include alkyl, alkenyl and alkinyl radicals. Preferred aliphatic radicals according to the present invention include but are not restricted to methyl, ethyl, vinyl (ethenyl), ethinyl, propyl, n-propyl, isopropyl, allyl (2-propenyl), 1-propinyl, methylethyl, butyl, n-butyl, iso-butyl, sec-butyl, tert-butyl butenyl, butinyl, 1-methylpropyl, 2-methylpropyl, 1,1-dimethylethyl, pentyl, n-pentyl, isopentyl, 1,1-dimethylpropyl, 1,2-dimethylpropyl, 2,2-dimethylpropyl, hexyl, 1-methylpentyl, n-heptyl, n-octyl, n-nonyl and n-decyl. Preferred substituents for aliphatic radicals, according to the present invention, are a $C_{1-6}$ alkyl group, cycloalkyl $C_{3-9}$ group, a linear or branched $C_{1-6}$ alkoxy group, —F, —Cl, —I, —Br, —CF$_3$, —CH$_2$F, —CHF$_2$, —CN, —OH, —SH, —NH$_2$, oxo, —(C=O)R', —SR', —SOR', —SO$_2$R', —NHR', —NR'R" whereby R' and optionally R" for each substitutent independently represents a linear or branched $C_{1-6}$-alkyl group.

Alkyl group/radicals, as referred to in the present invention, are saturated aliphatic radicals. They may be linear or branched and are optionally substituted. $C_{1-6}$ alkyl as expressed in the present invention means an alkyl radical of 1, 2, 3, 4, 5 or 6 carbon atoms.

Cycloalkyl group/radical $C_{3-9}$, as referred to in the present invention, are understood as meaning saturated and unsaturated (but not aromatic), cyclic hydrocarbons, which can optionally be unsubstituted, mono- or polysubstituted. In these radicals, for example $C_{3-4}$ cycloalkyl represents C3- or C4-cycloalkyl, $C_{3-6}$-cycloalkyl represents C3-, C4- or C5-cycloalkyl, etc. Mono- or polyunsaturated, preferably monounsaturated, cycloalkyls also in particular fall under the term cycloalkyl as long as the cycloalkyl is not an aromatic system. Examples for cycloalkyl radical preferably include but are not restricted to cyclopropyl, 2-methylcyclopropyl, cyclopropylmethyl, cyclobutyl, cyclopentyl, cyclopentylmethyl, cyclohexyl, cycloheptyl, cyclooctyl, acetyl, tert-butyl, adamantyl, noradamantyl. Cycloalkyl radicals $C_{3-9}$, as defined in the present invention, are optionally mono- or polysubstituted by substitutents independently selected from a $C_{1-6}$ alkyl group, a phenyl group, a benzyl group, a linear or branched $C_{1-6}$ alkoxy group, —F, —Cl, —I, —Br, —CF$_3$, —CH$_2$F, —CHF$_2$, —CN, —OH, —SH, —NH$_2$, oxo, —(C=O)R', —SR', —SOR', —SO$_2$R', —NHR', —NR'R" whereby R' and optionally R" for each substitutent independently represents a linear or branched $C_{1-6}$-alkyl group.

Heterocycloalkyl group/radical $C_{3-9}$, as referred to in the present invention, are understood as meaning saturated and unsaturated (but not aromatic), cyclic hydrocarbons having at least one heteroatom preferably selected from S, N or O and which can optionally be unsubstituted, mono- or polysubstituted. In these radicals, for example $C_{3-4}$ heterocycloalkyl represents C3- or C4-heterocycloalkyl, $C_{3-5}$-heterocycloalkyl represents C3-, C4- or C5-heterocycloalkyl, etc. Mono- or polyunsaturated, preferably monounsaturated heterocycloalkyls also in particular fall under the term heterocycloalkyl as long as the heterocycloalkyl is not an aromatic system. Examples for heterocycloalkyl radical preferably include but are not restricted to pyrroline, pyrrolidine, pyrrolidineone, pyrazoline, pyrazolinone, oxopyrazolinone, aziridine, azetidine, tetrahydropyrrole, oxirane, oxetane, dioxetane, tetrahydropyrane, tetrahydrofurane, tetrahydro-2H-thiopyran, dioxane, dioxolane, oxathiolane, oxazolidine, thiirane, thietane, thiolane, thiane, thiazolidine, piperidine, piperazine, morpholine or azepane. Heterocycloalkyl radicals $C_{3-9}$, as defined in the present invention, are optionally mono- or polysubstituted by substitutents independently selected from a $C_{1-6}$ alkyl group, a phenyl group, a benzyl group, a linear or branched $C_{1-6}$ alkoxy group, —F, —Cl, —I, —Br, —CF$_3$, —CH$_2$F, —CHF$_2$, —CN, —OH, —SH, —NH$_2$, oxo, —(C=O)R', —SR', —SOR', —SO$_2$R', —NHR', —NR'R" whereby R' and optionally R" for each substitutent independently represents a linear or branched $C_{1-6}$-alkyl group.

A cycloalkylalkyl group/radical $C_{1-10}$, as defined in the present invention, comprises a linear or branched, optionally at least mono-substituted alkyl chain of 1 to 10 atoms which is bonded to a cycloalklyl group, as defined above. The cycloalkylalkyl radical is bonded to the molecule through the alkyl chain. A preferred cycloalkyl-alkyl group/radical is a cyclopropyl methyl group, wherein the alkyl chain is optionally branched or substituted. Preferred substituents for cycloalkylalkyl group/radical, according to the present invention, are F, Cl, Br, I, NH$_2$, SH, OH, SO$_2$, CF$_3$, carboxy, amido, cyano, carbamyl, nitro, phenyl, benzyl, —SO$_2$NH$_2$, $C_{1-6}$ alkyl and/or $C_{1-6}$-alkoxy.

An aryl group/radical, as referred to in the present invention, is understood as meaning ring systems with at least one aromatic ring but without heteroatoms even in only one of the rings. These aryl radicals may optionally be mono- or polysubstituted by substitutents independently selected from a $C_{1-6}$ alkyl group, a linear or branched $C_{1-6}$ alkoxy group, an optionally at least mono-substituted phenyl group, —F, —Cl, —I, —Br, —CF$_3$, —CH$_2$F, —CHF$_2$, —CN, —OH, —SH, —NH$_2$, oxo, —(C=O)R', —SR', —SOR', -SO$_2$R', —N(C=O) OR', —NHR', —NR'R" whereby R' and optionally R" for each substitutent independently represents a linear or branched $C_{1-6}$-alkyl group. Preferred examples of aryl radicals include but are not restricted to phenyl, naphthyl, fluoranthenyl, fluorenyl, tetralinyl or indanyl or anthracenyl radicals, which may optionally be mono- or polysubstituted, if not defined otherwise.

An arylalkyl radical $C_{1-10}$, as defined in the present invention, comprises a linear or branched, optionally at least mono-substituted alkyl chain of 1 to 10 carbon atoms which is bonded to an aryl group, as defined above. The arylalkyl radical is bonded to the molecule through the alkyl chain. A preferred arylalkyl radical is a benzyl group, wherein the alkyl chain is optionally branched or substituted. Preferred substituents for arylalkyl radicals, according to the present invention, are F, Cl, Br, I, NH$_2$, SH, OH, SO$_2$, CF$_3$, carboxy, amido, cyano, carbamyl, nitro, phenyl, benzyl, —SO$_2$NH$_2$, $C_{1-6}$ alkyl and/or $C_{1-6}$ alkoxy.

A heteroaryl group/radical, is understood as meaning heterocyclic ring systems which have at least one aromatic ring and may optionally contain one or more heteroatoms from the group consisting of nitrogen, oxygen and/or sulfur and may optionally be mono- or polysubstituted by substitutents independently selected from a $C_{1-6}$ alkyl group, a linear or branched $C_{1-6}$ alkoxy group, F, Cl, I, Br, CF$_3$, CH$_2$F, CHF$_2$, CN, OH, SH, NH$_2$, oxo, (C=O)R', SR', SOR', SO$_2$R', NHR', NR'R" whereby R' and optionally R" for each substituent independently represents a linear or branched $C_{1-6}$ alkyl group. Preferred examples of heteroaryls include but are not restricted to furan, benzofuran, thiophene, benzothiophene, pyrrole, pyridine, pyrimidine, pyridazine, pyrazine, quinoline, isoquinoline, phthalazine, benzo-1,2,5-thiadiazole, benzothiazole, indole, benzotriazole, benzodioxolane, benzodioxane, benzimidzole, carbazole and quinazoline.

Heteroarylalkyl group/radical $C_{1-10}$ as defined in the present invention, comprises a linear or branched, optionally at least mono-substituted alkyl chain of 1 to 10 carbon atoms which is bonded to an heteroaryl group, as defined above. The heteroarylalkyl radical is bonded to the molecule through the alkyl chain. A preferred heteroarylalkyl radical is a methylpiridinyl group, wherein the alkyl chain is optionally branched or substituted. Preferred substituents for heteroarylalkyl radicals, according to the present invention, are F, Cl, Br, I, NH$_2$, SH, OH, SO$_2$, CF$_3$, carboxy, amido, cyano, carbamyl, nitro, phenyl, benzyl, —SO$_2$NH$_2$, $C_{1-6}$ alkyl and/or $C_{1-6}$ alkoxy.

The term "condensed" according to the present invention means that a ring or ring-system is attached to another ring or ring-system, whereby the terms "annulated" or "annelated" are also used by those skilled in the art to designate this kind of attachment.

The term "spirofused" or "spirofusion" means that a ring or ring system is attached to another ring or ring system through at least one spiro atom shared by either ring or ring system.

The term "ring system" according to the present invention refers to ring systems comprising saturated, unsaturated or aromatic carbocyclic ring systems which contain optionally at least one heteroatom as ring member and which are optionally at least mono-substituted. Said ring systems may be condensed to other carbocyclic ring systems such as aryl groups, naphtyl groups, heteroaryl groups, cycloalkyl groups, etc.

Cyclyl groups/radicals or cyclic systems, as defined in the present invention, comprise any saturated, unsaturated or aromatic carbocyclic ring systems which contain optionally at least one heteroatom as ring member and which are optionally at least mono-substituted. Cyclyl groups or cyclic systems preferably comprise aryl, heteroaryl, cyclyl, heterocyclyl and/or spiro ring systems.

Heterocyclyl groups/radicals or heterocyclic systems, as defined in the present invention, comprise any saturated, unsaturated or aromatic carbocyclic ring systems which are optionally at least mono-substituted and which contain at least one heteroatom as ring member. Preferred heteroatoms for these heterocyclyl groups are N, S or O. Preferred substituents for heterocyclyl radicals, according to the present invention, are F, Cl, Br, I, $NH_2$, SH, OH, $SO_2$, $CF_3$, carboxy, amido, cyano, carbamyl, nitro, phenyl, benzyl, —$SO_2NH_2$, $C_{1-6}$ alkyl and/or $C_{1-6}$-alkoxy.

The term "salt" is to be understood as meaning any form of the active compound according to the invention in which this assumes an ionic form or is charged and is coupled with a counter-ion (a cation or anion) or is in solution. By this are also to be understood complexes of the active compound with other molecules and ions, in particular complexes which are formed via ionic interactions.

The term "physiologically acceptable salt" is understood in particular, in the context of this invention, as salt (as defined above) formed either with a physiologically tolerated acid, that is to say salts of the particular active compound with inorganic or organic acids which are physiologically tolerated—especially if used on humans and/or mammals—or with at least one, preferably inorganic, cation which are physiologically tolerated—especially if used on humans and/or mammals. Examples of physiologically tolerated salts of particular acids are salts of: hydrochloric acid, hydrobromic acid, sulfuric acid, hydrobromide, monohydrobromide, monohydrochloride or hydrochloride, methiodide, methanesulfonic acid, formic acid, acetic acid, oxalic acid, succinic acid, malic acid, tartaric acid, mandelic acid, fumaric acid, lactic acid, citric acid, glutamic acid, hippuric acid picric acid and/or aspartic acid. Examples of physiologically tolerated salts of particular bases are salts of alkali metals and alkaline earth metals and with $NH_4$.

The term "solvate" is to be understood as meaning any form of the active compound according to the invention in which this compound has attached to it via non-covalent binding another molecule (most likely a polar solvent) especially including hydrates and alcoholates, e.g. methanolate.

The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the compounds of the invention: esters, amino acid esters, phosphate esters, metal salts sulfonate esters, carbamates, and amides. Examples of well known methods of producing a prodrug of a given active compound are known to those skilled in the art and can be found e.g. in Krogsgaard-Larsen et al. "Textbook of Drug design and Discovery" Taylor & Francis (April 2002).

Any compound that is a prodrug of a compound of formula (I) is within the scope of the invention. Particularly favored prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

In a particular and preferred embodiment of the invention $R_1$ represents a group selected from:

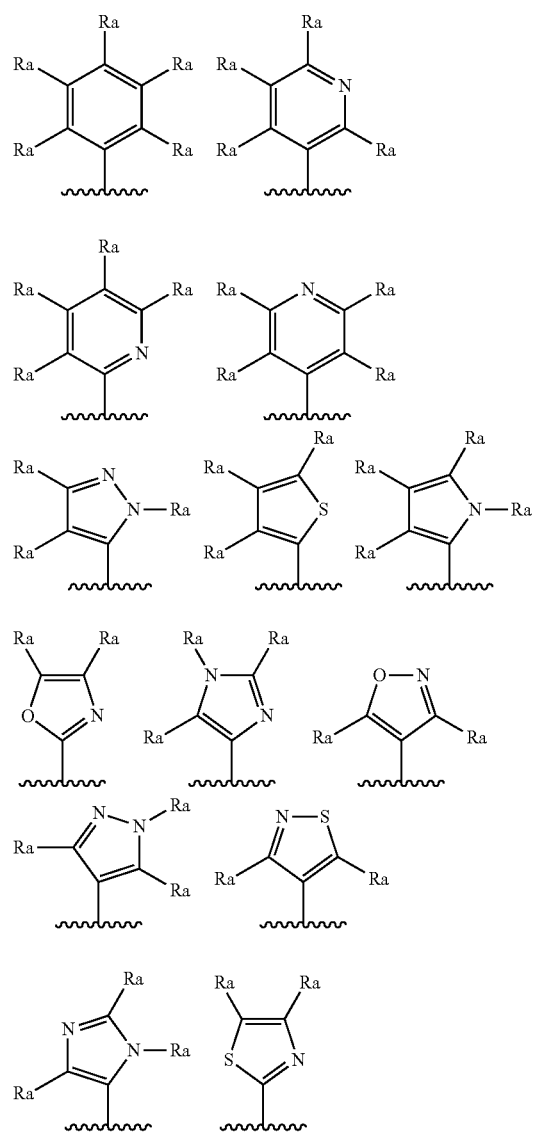

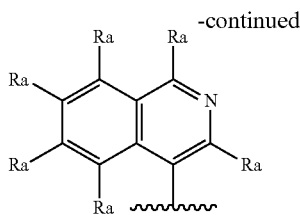

where Ra independently represents a hydrogen atom, an alkyl radical $C_1$-$C_6$, a halogen atom, an haloalkyl radical $C_1$-$C_6$, —CN, —OR or —$SO_2$R where R is selected from hydrogen or an alkyl radical $C_1$-$C_6$.

In another preferred embodiment $R_2$ and $R_3$ independently represent a branched or unbranched, saturated or unsaturated, optionally at least mono-substituted, aliphatic radical $C_{1-10}$; a substituted or unsubstituted aryl radical; a substituted or unsubstituted, branched or unbranched arylalkyl radical $C_{1-10}$.

In a still more preferred embodiment $R_2$ and $R_3$ together with the bridging nitrogen form a substituted or unsubstituted heterocycloalkyl radical $C_{3-9}$; or a substituted or unsubstituted heteroaryl radical $C_{3-9}$.

The more preferred embodiment of the invention is that in which $R_2$ and $R_3$ together with the bridging nitrogen form a piperidine which is optionally substituted by at least one halogen atom.

In an additional particular and preferred embodiment n is 2 in compounds of formula (I).

In preferred variants of the invention, the sigma ligand of formula (I) is selected from:
4-phenyl-1-(2-(piperidin-1-yl)ethyl)-1H-pyrazolo[3,4-d]pyrimidine
1-(2-(piperidin-1-yl)ethyl)-4-o-tolyl-1H-pyrazolo[3,4-d]pyrimidine
1-(2-(piperidin-1-yl)ethyl)-4-m-tolyl-1H-pyrazolo[3,4-d]pyrimidine hydrochloride
1-(2-(piperidin-1-yl)ethyl)-4-(pyridin-3-yl)-1H-pyrazolo[3,4-d]pyrimidine
4-(2-methylpyridin-3-yl)-1-(2-(piperidin-1-yl)ethyl)-1H-pyrazolo[3,4-d]pyrimidine
3,5-dimethyl-4-(1-(2-(piperidin-1-yl)ethyl)-1H-pyrazolo[3,4-d]pyrimidin-4-yl)isoxazole hydrochloride
4-(4-methoxypyridin-3-yl)-1-(2-(piperidin-1-yl)ethyl)-1H-pyrazolo[3,4-d]pyrimidine hydrochloride
4-(4-methylpyridin-3-yl)-1-(2-(piperidin-1-yl)ethyl)-1H-pyrazolo[3,4-d]pyrimidine hydrochloride
4-(1-methyl-1H-pyrazol-5-yl)-1-(2-(piperidin-1-yl)ethyl)-1H-pyrazolo[3,4-d]pyrimidine
4-(2-methoxypyridin-3-yl)-1-(2-(piperidin-1-yl)ethyl)-1H-pyrazolo[3,4-d]pyrimidine
4-(2-methoxypyridin-3-yl)-1-(2-(piperidin-1-yl)ethyl)-1H-pyrazolo[3,4-d]pyrimidine (L)-tartrate
4-(1-(2-(piperidin-1-yl)ethyl)-1H-pyrazolo[3,4-d]pyrimidin-4-yl)isoquinoline
4-(2-ethoxyphenyl)-1-(2-(piperidin-1-yl)ethyl)-1H-pyrazolo[3,4-d]pyrimidine hydrochloride
4-(4-fluorophenyl)-1-(2-(piperidin-1-yl)ethyl)-1H-pyrazolo[3,4-d]pyrimidine
4-(4-methoxyphenyl)-1-(2-(piperidin-1-yl)ethyl)-1H-pyrazolo[3,4-d]pyrimidine
4-(1-methyl-3-(trifluoromethyl)-1H-pyrazol-5-yl)-1-(2-(piperidin-1-yl)ethyl)-1H-pyrazolo[3,4-d]pyrimidine
4-(1-(2-(piperidin-1-yl)ethyl)-1H-pyrazolo[3,4-d]pyrimidin-4-yl)benzonitrile
4-(5-methylpyridin-3-yl)-1-(2-(piperidin-1-yl)ethyl)-1H-pyrazolo[3,4-d]pyrimidine
1-(2-(piperidin-1-yl)ethyl)-4-(pyridin-2-yl)-1H-pyrazolo[3,4-d]pyrimidine
4-(5-chlorothiophen-2-yl)-1-(2-(piperidin-1-yl)ethyl)-1H-pyrazolo[3,4-d]pyrimidine
4-(4-chlorophenyl)-1-(2-(piperidin-1-yl)ethyl)-1H-pyrazolo[3,4-d]pyrimidine
4-(6-methylpyridin-2-yl)-1-(2-(piperidin-1-yl)ethyl)-1H-pyrazolo[3,4-d]pyrimidine
4-(4-(methylsulfonyl)phenyl)-1-(2-(piperidin-1-yl)ethyl)-1H-pyrazolo[3,4-d]pyrimidine
1-(2-(piperidin-1-yl)ethyl)-4-(1H-pyrazol-4-yl)-1H-pyrazolo[3,4-d]pyrimidine
4-(2-chloro-5-methylphenyl)-1-(2-(piperidin-1-yl)ethyl)-1H-pyrazolo[3,4-d]pyrimidine
4-(2,5-dimethylphenyl)-1-(2-(piperidin-1-yl)ethyl)-1H-pyrazolo[3,4-d]pyrimidine
4-(1-methyl-1H-pyrrol-2-yl)-1-(2-(piperidin-1-yl)ethyl)-1H-pyrazolo[3,4-d]pyrimidine
4-(4-fluoro-2-methoxyphenyl)-1-(2-(piperidin-1-yl)ethyl)-1H-pyrazolo[3,4-d]pyrimidine
4-(4-fluoro-2-methylphenyl)-1-(2-(piperidin-1-yl)ethyl)-1H-pyrazolo[3,4-d]pyrimidine
4-(1-methyl-1H-imidazol-4-yl)-1-(2-(piperidin-1-yl)ethyl)-1H-pyrazolo[3,4-d]pyrimidine
4-(1-methyl-1H-pyrazol-4-yl)-1-(2-(piperidin-1-yl)ethyl)-1H-pyrazolo[3,4-d]pyrimidine
2-(1-(2-(piperidin-1-yl)ethyl)-1H-pyrazolo[3,4-d]pyrimidin-4-yl)oxazole
2-(1-(2-(piperidin-1-yl)ethyl)-1H-pyrazolo[3,4-d]pyrimidin-4-yl)thiazole
4-(4-fluoro-2-(trifluoromethyl)phenyl)-1-(2-(piperidin-1-yl)ethyl)-1H-pyrazolo[3,4-d]pyrimidine
4-(2-chlorophenyl)-1-(2-(piperidin-1-yl)ethyl)-1H-pyrazolo[3,4-d]pyrimidine
4-(1-(2-(piperidin-1-yl)ethyl)-1H-pyrazolo[3,4-d]pyrimidin-4-yl)isothiazole
4-(1-isopropyl-1H-pyrazol-4-yl)-1-(2-(piperidin-1-yl)ethyl)-1H-pyrazolo[3,4-d]pyrimidine
1-(2-(piperidin-1-yl)ethyl)-4-(2-(trifluoromethyl)phenyl)-1H-pyrazolo[3,4-d]pyrimidine
4-(2,4-difluorophenyl)-1-(2-(piperidin-1-yl)ethyl)-1H-pyrazolo[3,4-d]pyrimidine
1-(2-(piperidin-1-yl)ethyl)-4-(pyridin-4-yl)-1H-pyrazolo[3,4-d]pyrimidine
4-(1-methyl-1H-imidazol-5-yl)-1-(2-(piperidin-1-yl)ethyl)-1H-pyrazolo[3,4-d]pyrimidine
4-(2-chloro-4-fluorophenyl)-1-(2-(piperidin-1-yl)ethyl)-1H-pyrazolo[3,4-d]pyrimidine
4-(2-chlorophenyl)-1-(2-(4,4-difluoropiperidin-1-yl)ethyl)-1H-pyrazolo[3,4-d]pyrimidine
4-(2-chloro-4-fluorophenyl)-1-(2-(4,4-difluoropiperidin-1-yl)ethyl)-1H-pyrazolo[3,4-d]pyrimidine
4-(4-chloro-2-fluorophenyl)-1-(2-(4,4-difluoropiperidin-1-yl)ethyl)-1H-pyrazolo[3,4-d]pyrimidine
4-(4-chloro-2-fluorophenyl)-1-(2-(piperidin-1-yl)ethyl)-1H-pyrazolo[3,4-d]pyrimidine
2-(4-(2-chlorophenyl)-1H-pyrazolo[3,4-d]pyrimidin-1-yl)-N-(4-fluorobenzyl)-N-methylethanamine
N-(4-fluorobenzyl)-N-methyl-2-(4-(1-methyl-1H-pyrazol-5-yl)-1H-pyrazolo[3,4-d]pyrimidin-1-yl)ethanamine
2-(4-(2-chloro-4-fluorophenyl)-1H-pyrazolo[3,4-d]pyrimidin-1-yl)-N-(4-fluorobenzyl)-N-methylethanamine
or their pharmaceutically acceptable salts, stereoisomers, solvates or a prodrug thereof.

Any compound referred to herein is intended to represent such specific compound as well as certain variations or forms. In particular, compounds referred to herein may have asymmetric centers and therefore exist in different enantiomeric or diastereomeric forms. Thus, any given compound referred to herein is intended to represent any one of a racemate, one or more enantiomeric forms, one or more diastereomeric forms, and mixtures thereof. Likewise, stereoisomerism or geometric isomerism about the double bond is also possible, therefore in some cases the molecule could exist as (E)-isomer or (Z)-isomer (trans and cis isomers). If the molecule contains several double bonds, each double bond will have its own stereoisomerism, that could be the same as, or different to, the stereoisomerism of the other double bonds of the molecule. Furthermore, compounds referred to herein may exist as atropisomers. All the stereoisomers including enantiomers, diastereoisomers, geometric isomers and atropisomers of the compounds referred to herein, and mixtures thereof, are considered within the scope of the present invention.

Furthermore, any compound referred to herein may exist as tautomers. Specifically, the term tautomer refers to one of two or more structural isomers of a compound that exist in equilibrium and are readily converted from one isomeric form to another. Common tautomeric pairs are amine-imine, amide-imidic acid, keto-enol, lactam-lactim, etc.

Unless otherwise stated, the compounds of the invention are also meant to include isotopically-labelled forms i.e. compounds which differ only in the presence of one or more isotopically-enriched atoms. For example, compounds having the present structures except for the replacement of at least one hydrogen atom by a deuterium or tritium, or the replacement of at least one carbon by $^{13}C$- or $^{14}C$-enriched carbon, or the replacement of at least one nitrogen by $^{15}N$-enriched nitrogen are within the scope of this invention.

The compounds of formula (I) or their salts or solvates are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I), or of its salts, solvates or prodrugs.

A specific embodiment of the invention is that in which the substituted pyrazolo[3,4-d]pyrimidine compounds of the invention represent a compound with the general formula (Ia):

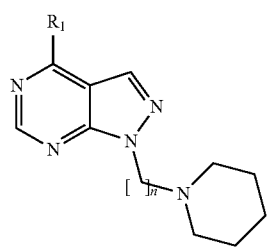
(Ia)

Still another specific embodiment of the invention is represented by compounds of general formula (Ib):

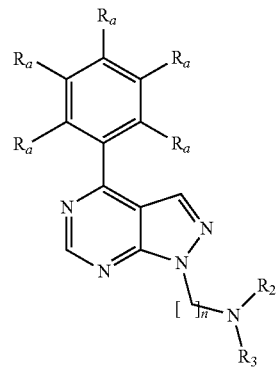
(Ib)

In another aspect, the invention refers to the processes for obtaining the compounds of general formula (I):

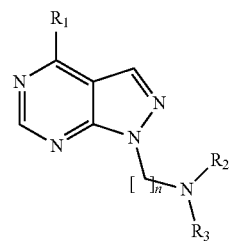
(I)

comprising the reaction between a compound of general formula (III):

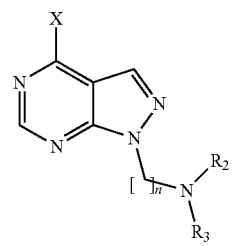
(III)

with a boronic acid of formula (V):

  (V)

R$_1$B(OH)$_2$ a corresponding ester or a corresponding organoborane, or with an organotin derivative of formula (VI):

R$_1$Sn(R$_4$)$_3$  (VI)

where R$_1$, R$_2$, R$_3$ and n have the meanings as in claim 1, X is a halogen atom and R$_4$ represents a C$_1$-C$_{10}$ alkyl radical.

The reaction for the synthesis of compounds of formula (I) is preferably a Palladium-catalysed cross-coupling reaction between a compound of general formula (III) with organometallic derivatives, such as boronic acids or esters (V) or with other organoboron reagents such as potassium organotrifluoroborates. The catalyst used are palladium complexes such as Pd(PPh$_3$)$_4$, Pd(dppf)Cl$_2$CH$_2$Cl$_2$, Pd(AcO)$_2$/S-Phos or Pd(OAc)$_2$/PPh$_3$. The reaction is carried out in solvents such as benzene, toluene, xylene, mesitylene, DMF, THF, DME, dioxane, n-butanol, methanol, ethanol, acetonitrile and water or a mixture of them and, preferably, in the presence of a base such as $Cs_2CO_3$, $Na_2CO_3$, $NaHCO_3$, $K_2CO_3$, KF, $K_3PO_4$, triethylamine, diisopropylethylamine, KOH or NaOH. The reaction is preferably carried out at a temperature range of 50° C. and the boiling point of the solvent or in a microwave reactor.

Compounds of formula (I) can also be prepared through the Palladium-catalysed cross-coupling reaction of a compound of general formula (III) with an organotin derivative of formula (VI). This reaction is carried out with palladium complexes such as $Pd(PPh_3)_4$, $Pd_2dba_3/P(2\text{-furyl})_3$, $Pd(OAc)_2/PPh_3$, $Pd(OAc)_2/P(2\text{-furyl})_3$, $Pd(OAc)_2/P\text{-t-Bu}_3$ or $Pd(OAc)_2/AsPh_3$ in solvents such as benzene, toluene, xylene, mesitylene, DMF, THF, NMP, DMSO, dioxane, chloroform or a mixture of them. The reaction is preferably carried out at a temperature range from 35° C. to the boiling point of the solvent or in a microwave reactor. The reaction can be carried out by adding additives such as CuI, CuCl, CuI, Cu(I) thiophenecarboxylate, triethylamine, diisopropylethylamine, $Cs_2CO_3$, NaOH, KF or CsF.

In turn, compounds of formula (III):

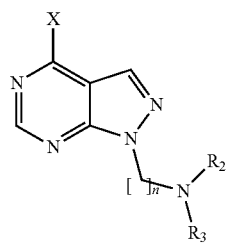

(III)

are prepared by a process comprising the reaction between a compound of general formula (II):

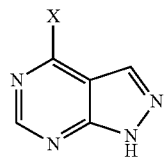

(II)

with a compound of formula general (IV):

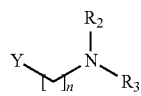

(IV)

where $R_2$, $R_3$ and n have the meanings as in general formula (I) and X is a halogen atom or triflate and Y is a suitable leaving group such as a halogen atom or a hydroxyl group.

Compounds of formula (III) can be prepared by two different processes. In a first process they are prepared by reaction between compounds of formula (II) with a compound of formula (IV) where Y is a suitable leaving group such as a halogen atom. When Y is a halogen atom the reaction is preferably carried out in an aprotic solvent such as dimethylformamide (DMF) in the presence of an inorganic base such as NaH.

When Y is a hydroxyl group the reaction is performed under so called Mitsunobu conditions, which involve the use of diethylazodicarboxylate, bis(1,1-dimethylethyl)azodicarboxylate or diisopropylazodicarboxylate and triphenylphosphine, providing an intermediate that binds to the hydroxyl group, activating it to a good leaving group, which is then displaced by the anion of compound (II). The reaction is preferentially carried out in a suitable solvent such as THF and at a temperature range from 0° C. to room temperature.

The general synthetic route for the preparation of compounds of general formula (I) is represented in scheme 1:

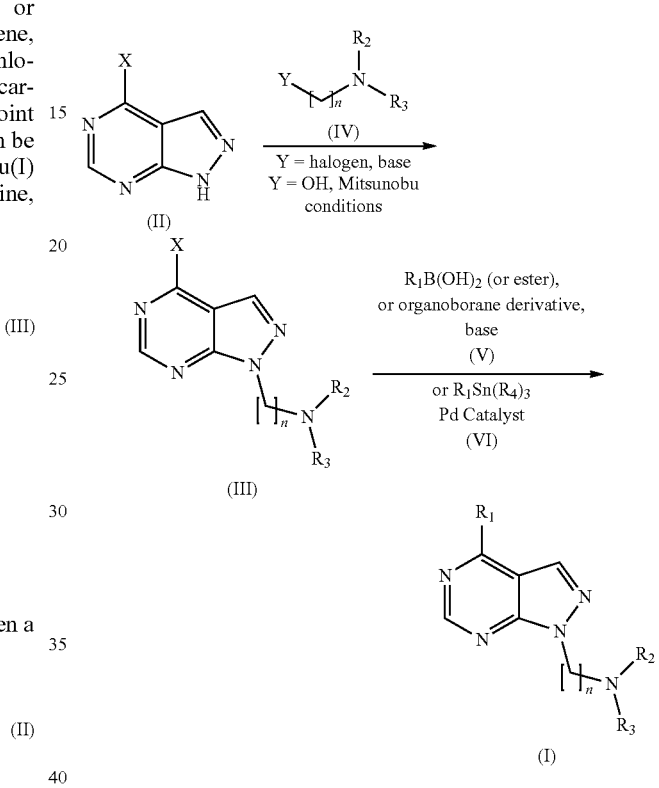

An additional aspect of the invention relates to the therapeutic use of the compounds of general formula (I). As mentioned above, compounds of general formula (I) show a strong affinity to sigma receptors and can behave as agonists, antagonists, inverse agonists, partial antagonists or partial agonists thereof. Therefore, compounds of general formula (I) are useful as medicaments.

They are suitable for the treatment and the prophylaxis of disorders and diseases mediated by sigma receptors, especially, sigma-1 receptors. In this sense, compounds of formula (I) are very good anxiolitic and immunosuppressant and are very useful in the treatment and prophylaxis of diarrhea, lipoprotein disorders, hyperlipidemia, hypertriglyceridemia, hypercholesterolemia, obesity, migraine, arthritis, hypertension, arrhythmia, ulcer, glaucoma, learning, memory and attention deficits, cognition disorders, neurodegenerative diseases, demyelinating diseases, addiction to drugs and chemical substances including cocaine, amphetamine, ethanol and nicotine; tardive diskinesia, ischemic stroke, epilepsy, stroke, stress, cancer, psychotic conditions, in particular depression, anxiety or schizophrenia; inflammation or autoimmune diseases.

The compounds of formula (I) are especially suited for the treatment of pain, especially neuropathic pain, inflammatory pain or other pain conditions involving allodynia and/or hyperalgesia. PAIN is defined by the International Association for the Study of Pain (IASP) as "an unpleasant sensory and emotional experience associated with actual or potential tissue damage, or described in terms of such damage (IASP, Classification of chronic pain, 2nd Edition, IASP Press (2002), 210). Even though pain is always subjective its causes or syndromes can be classified.

In a preferred embodiment compounds of the invention are used for the treatment and prophylaxis of allodynia and more specifically mechanical or thermal allodynia.

In another preferred embodiment compounds of the invention are used for the treatment and prophylaxis of hyperalgesia.

In yet another preferred embodiment compounds of the invention are used for the treatment and prophylaxis of neuropathic pain and more specifically for the treatment and prophylaxis of hyperpathia.

A related aspect of the invention refers to the use of compounds of formula (I) for the manufacture of a medicament for the treatment of disorders and diseases mediated by sigma receptors, as explained before.

Another aspect of the invention is a pharmaceutical composition which comprises at least a compound of general formula (I) or a pharmaceutically acceptable salt, prodrug, isomer or solvate thereof, and at least a pharmaceutically acceptable carrier, additive, adjuvant or vehicle.

The pharmaceutical composition of the invention can be formulated as a medicament in different pharmaceutical forms comprising at least a compound binding to the sigma receptor and optionally at least one further active substance and/or optionally at least one auxiliary substance.

The auxiliary substances or additives can be selected among carriers, excipients, support materials, lubricants, fillers, solvents, diluents, colorants, flavour conditioners such as sugars, antioxidants and/or agglutinants. In the case of suppositories, this may imply waxes or fatty acid esters or preservatives, emulsifiers and/or carriers for parenteral application. The selection of these auxiliary materials and/or additives and the amounts to be used will depend on the form of application of the pharmaceutical composition.

The pharmaceutical composition in accordance with the invention can be adapted to any form of administration, be it orally or parenterally, for example pulmonarily, nasally, rectally and/or intravenously.

Preferably, the composition is suitable for oral or parenteral administration, more preferably for oral, intravenous, intraperitoneal, intramuscular, subcutaneous, intrathekal, rectal, transdermal, transmucosal or nasal administration.

The composition of the invention can be formulated for oral administration in any form preferably selected from the group consisting of tablets, drageés, capsules, pills, chewing gums, powders, drops, gels, juices, syrups, solutions and suspensions.

The composition of the present invention for oral administration may also be in the form of multiparticulates, preferably microparticles, microtablets, pellets or granules, optionally compressed into a tablet, filled into a capsule or suspended in a suitable liquid. Suitable liquids are known to those skilled in the art.

Suitable preparations for parenteral applications are solutions, suspensions, reconstitutable dry preparations or sprays.

The compounds of the invention can be formulated as deposits in dissolved form or in patches, for percutaneous application.

Skin applications include ointments, gels, creams, lotions, suspensions or emulsions.

The preferred form of rectal application is by means of suppositories.

The respective medicament may—depending on its route of administration—also contain one or more auxiliary substances known to those skilled in the art. The medicament according to the present invention may be produced according to standard procedures known to those skilled in the art.

The daily dosage for humans and animals may vary depending on factors that have their basis in the respective species or other factors, such as age, sex, weight or degree of illness and so forth. The daily dosage for humans may preferably be in the range from 1 to 2000, preferably 1 to 1500, more preferably 1 to 1000 milligrams of active substance to be administered during one or several intakes per day.

Described below are a number of examples by way of illustration of the invention and do not limit it in anyway.

Synthesis of Intermediates of General Formal (III)

Synthesis of 4-chloro-1-(2-(piperidin-1-yl)ethyl)-1H-pyrazolo[3,4-d]pyrimidine

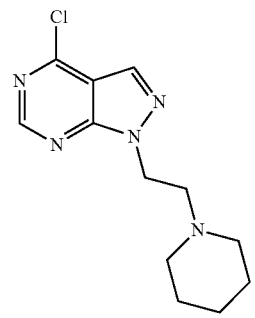 [SMILES: Clc1ncnc2c1cnn2CCN1CCCCC1]

To a stirred solution of 4-chloro-1H-pyrazolo[3,4-d]pyrimidine (0.2 g, 1.29 mmol) in anh THF (10 mL), 2-(piperidin-1-yl)ethanol (0.258 mL, 1.94 mmol) and triphenylphosphine (0.51 g, 1.94 mmol) were sequentially added. The reaction mixture was cooled to 0° C. and diisopropylazodicarboxylate (0.38 mL, 1.94 mmol) was added dropwise. The mixture was stirred for 30 min. at 0° C. and kept overnight at 4° C. The solvent was removed at reduced pressure and the residue was dissolved in DCM and washed with diluted HCl 1N. The aqueous phase was separated, basified and extracted with DCM. The organic phase was separated, dried and the solvent was removed under reduced pressure to give a residue that was purified by flash chromatography eluting with (EtOAc/Petroleum ether, 8:2) to yield 4-chloro-1-(2-(piperidin-1-yl)ethyl)-1H-pyrazolo[3,4-d]pyrimidine (146 mg, 55 mmol, 42%) as an oil that solidifies "on standing".

The following intermediates were also prepared following the above procedure:

4-chloro-1-(2-(4,4-difluoropiperidin-1-yl)ethyl)-1H-pyrazolo[3,4-d]pyrimidine 2-(4-chloro-1H-pyrazolo[3,4-d]pyrimidin-1-yl)-N-(4-fluorobenzyl)-N-methylethanamine

Synthesis of Compounds of General Formula (I)

The specific compounds falling within general formula (I) were prepared following three different methodologies which are represented as method A, B and C

Method A

Example 1

Synthesis of 4-phenyl-1-(2-(piperidin-1-yl)ethyl)-1H-pyrazolo[3,4-d]pyrimidine

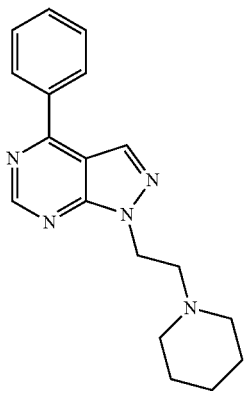 [SMILES: c1ccc(-c2ncnc3c2cnn3CCN2CCCCC2)cc1]

A mixture of 4-chloro-1-(2-(piperidin-1-yl)ethyl)-1H-pyrazolo[3,4-d]pyrimidine (50 mg, 0.19 mmol), phenylboronic acid (73 mg, 0.60 mmol) and anhydrous $K_2CO_3$ (82 mg, 0.59 mmol) in toluene (3 mL) was introduced in a microwave vial. It was degassed by argon for 30 minutes followed by the addition of Pd(PPh$_3$)$_4$ (4.0 mg, 0.003 mmol) after which the mixture was degassed for 10 additional minutes. The mixture was stirred at 150° C. for 30 min under microwave irradiation (150 W). After cooling to rt, the mixture was filtered on decalite and the solvent was removed at reduced pressure. The crude was purified by flash chromatography to provide 4-phenyl-1-(2-(piperidin-1-yl)ethyl)-1H-pyrazolo[3,4-d]pyrimidine as a white solid (19.1 mg, 0.06 mmol, 33%).

Method B

Example 32

Synthesis of 2-(1-(2-(piperidin-1-yl)ethyl)-1H-pyrazolo[3,4-d]pyrimidin-4-yl)oxazole

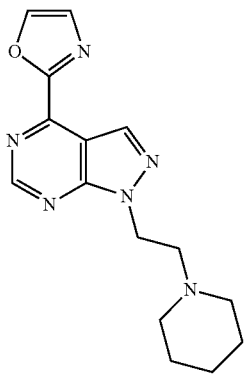

A mixture of 4-chloro-1-(2-(piperidin-1-yl)ethyl)-1H-pyrazolo[3,4-d]pyrimidine (50 mg, 0.188 mmol), 2-(tri-n-butylstannyl)oxazole (0.059 ml, 0.282 mmol) in toluene (3 mL) was introduced in a microwave vial. It was degassed by argon for 30 minutes followed by the addition of Pd(Ph3P)4 (22 mg, 19 mmol) after which the mixture was degassed for 10 additional minutes. The mixture was stirred at 100° C. for 30 min under microwave irradiation (150 W). The solvent was removed and the crude thus obtained was purified by flash chromatography to provide 2-(1-(2-(piperidin-1-yl)ethyl)-1H-pyrazolo[3,4-d]pyrimidin-4-yl)oxazole as a cream-colored solid (37 mg, 0.12 mmol, 66%).

Method C

Example 11

Synthesis of 4-(2-Methoxypyridin-3-Yl)-1-(2-(Piperidin-1-yl)ethyl)-1H-pyrazolo[3,4-d]pyrimidine (L)-tartrate

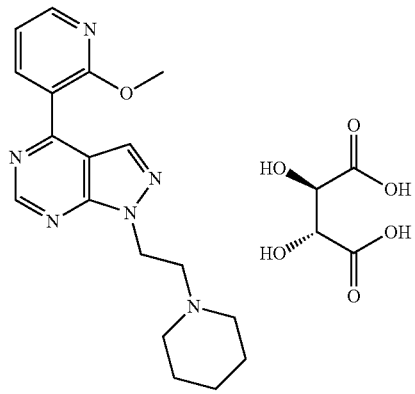 [SMILES: COc1ncccc1-c1ncnc2c1cnn2CCN1CCCCC1 ; O=C(O)[C@H](O)[C@@H](O)C(=O)O]

(L)-Tartaric acid (15 mg, 0.10 mmol) was added to a solution of 4-(2-methoxypyridin-3-yl)-1-(2-(piperidin-1-yl)ethyl)-1H-pyrazolo[3,4-d]pyrimidine (30 mg, 0.09 mmol) in MeOH (1 mL) and the suspension was stirred at room temperature for 2 h. The solvent was removed under reduced pressure and the residue was grinded and washed with diethylether three times. The solid thus obtained was dried to give 4-(2-methoxypyridin-3-yl)-1-(2-(piperidin-1-yl)ethyl)-1H-pyrazolo[3,4-d]pyrimidine (L)-tartrate as a white solid (35 mg, 0.07 mmol, 80%).

The following compounds where prepared according to the methods described above as specified in each case. The hydrochloride salts of examples 3, 6, 7, 8 and 13 were prepared according to the method C but with HCl instead of (L)-Tartaric acid.

| Example | Structure | Name | Method | NMR |
|---|---|---|---|---|
| 1 | 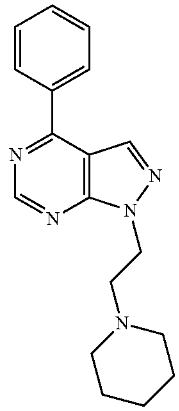 [SMILES: c1ccc(-c2ncnc3c2cnn3CCN2CCCCC2)cc1] | 4-phenyl-1-(2-(piperidin-1-yl)ethyl)-1H-pyrazolo[3,4-d]pyrimidine | A | ¹H NMR (CDCl₃) δ: 9.07 (s, 1H), 8.37 (s, 1H), 8.19 (dd, J = 6.3, 2.2 Hz, 2H), 7.63-7.56 (m, 3H), 4.82 (t, J = 6.7 Hz, 2H), 3.14 (t, J = 7.1 Hz, 2H), 2.80-2.60 (m, 4H), 1.75-1.60 (m, 4H), 1.51-1.41 (m, 2H). |
| 2 | 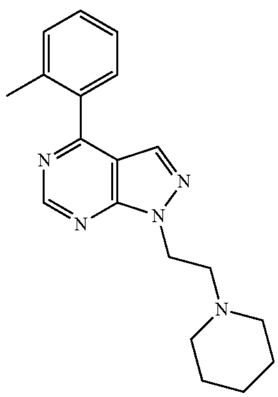 [SMILES: Cc1ccccc1-c1ncnc2c1cnn2CCN1CCCCC1] | 1-(2-(piperidin-1-yl)ethyl)-4-o-tolyl-1H-pyrazolo[3,4-d]pyrimidine | A | ¹H NMR (CDCl₃) δ: 9.07 (s, 1H), 8.00 (s, 1H), 7.53 (d, J = 7.3 Hz, 1H), 7.48-7.30 (m, 3H), 4.67 (t, J = 7.2 Hz, 2H), 2.92 (t, J = 7.2 Hz, 2H), 2.58-2.46 (m, 4H), 2.43 (s, 3H), 1.62-1.48 (m, 4H), 1.48-1.37 (m, 2H). |
| 3 | 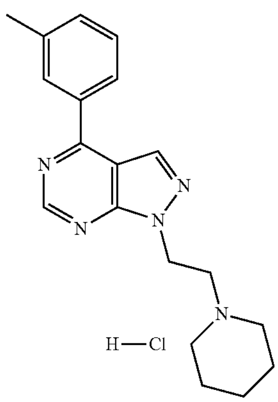 | 1-(2-(piperidin-1-yl)ethyl)-4-m-tolyl-1H-pyrazolo[3,4-d]pyrimidine hydrochloride | A then C | ¹H NMR (CDCl₃) δ 12.72 (bs, 1H), 9.12 (s, 1H), 8.44 (s, 1H), 8.08-7.94 (m, 2H), 7.58-7.38 (m, 2H), 5.34-4.99 (m, 2H), 3.84-3.50 (m, 4H), 2.91-2.57 (m, 2H), 2.50 (s, 3H), 1.99-1.71 (m, 4H), 0.99-0.71 (m, 2H). |
| 4 | 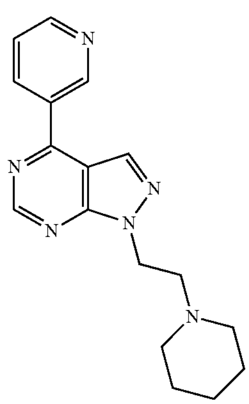 [SMILES: c1cncc(-c2ncnc3c2cnn3CCN2CCCCC2)c1] | 1-(2-(piperidin-1-yl)ethyl)-4-(pyridin-3-yl)-1H-pyrazolo[3,4-d]pyrimidine | A | ¹H NMR (CDCl₃) δ: 9.43 (d, J = 1.6 Hz, 1H), 9.09 (s, 1H), 8.81 (dd, J = 4.8, 1.6 Hz, 1H), 8.52 (dt, J = 7.9, 1.9 Hz, 1H), 8.37 (s, 1H), 7.55 (dd, J = 7.9, 4.8 Hz, 1H), 4.69 (t, J = 7.0 Hz, 2H), 2.92 (t, J = 7.0 Hz, 2H), 2.61-2.38 (m, 4H), 1.62-1.45 (m, 4H), 1.45-1.31 (m, 2H). |

-continued

| Example | Structure | Name | Method | NMR |
|---|---|---|---|---|
| 5 | 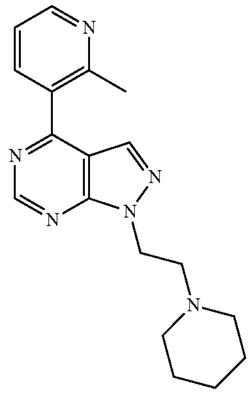 [SMILES: Cc1ncccc1-c1ncnc2c1cnn2CCN1CCCCC1] | 4-(2-methylpyridin-3-yl)-1-(2-(piperidin-1-yl)ethyl)-1H-pyrazolo[3,4-d]pyrimidine | A | $^1$H NMR (CDCl$_3$) δ: 9.09 (s, 1H), 8.68 (dd, J = 4.9, 1.8 Hz, 1H), 7.98 (s, 1H), 7.85 (dd, J = 7.7, 1.8 Hz, 1H), 7.33 (dd, J = 7.7, 4.9 Hz, 1H), 4.68 (t, J = 7.1 Hz, 2H), 2.91 (t, J = 7.1 Hz, 2H), 2.65 (s, 3H), 2.55-2.45 (m, 4H), 1.58-1.46 (m, 4H), 1.47-1.35 (m, 2H). |
| 6 | 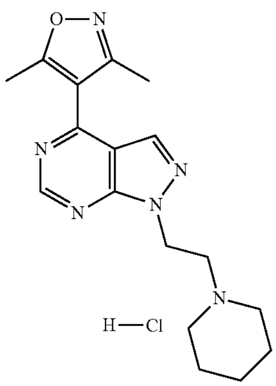 | 3,5-dimethyl-4-(1-(2-(piperidin-1-yl)ethyl)-1H-pyrazolo[3,4-d]pyrimidin-4-yl)isoxazole hydrochloride | A then C | $^1$H NMR (CDCl$_3$) δ 12.72 (bs, 1H), 9.10 (s, 1H), 8.11 (s, 1H), 5.34-4.95 (m, 2H), 3.98-3.50 (m, 4H), 2.89-2.66 (m, 2H), 2.63 (s, 3H), 2.47 (s, 3H), 1.56-1.19 (m, 4H), 0.99-0.73 (m, 2H). |
| 7 | 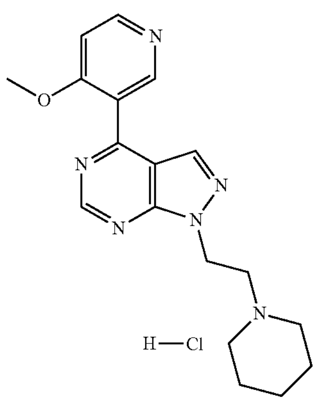 | 4-(4-methoxypyridin-3-yl)-1-(2-(piperidin-1-yl)ethyl)-1H-pyrazolo[3,4-d]pyrimidine hydrochloride | A then C | $^1$H NMR (CD$_3$OD) δ 9.18 (s, 1H), 9.10 (s, 1H), 8.89 (d, J = 7.20 Hz, 1H), 8.41 (s, 1H), 7.86 (d, J = 6.88 Hz, 1H), 5.03 (t, J = 6.02 Hz, 2H), 4.26 (s, 3H), 3.91-3.65 (m, 4H), 3.10 (t, J = 12.16 Hz, 3H), 1.99-1.67 (m, 5H), 1.68-1.43 (m, 1H). |
| 8 | 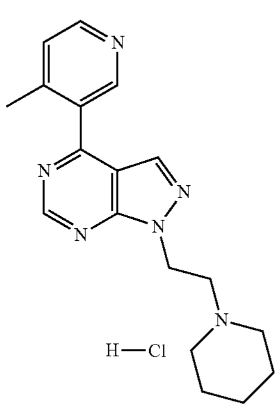 | 4-(4-methylpyridin-3-yl)-1-(2-(piperidin-1-yl)ethyl)-1H-pyrazolo[3,4-d]pyrimidine hydrochloride | A then C | $^1$H NMR (CD$_3$OD) δ 9.23 (s, 1H), 9.14 (s, 1H), 8.92 (d, J = 6.00 Hz, 1H), 8.45 (s, 1H), 8.21 (d, J = 6.10 Hz, 1H), 5.06 (t, J = 5.93 Hz, 2H), 3.92-3.67 (m, 4H), 3.10 (t, J = 11.77 Hz, 2H), 2.78 (s, 3H), 1.58-1.18 (m, 4H), 1.09-0.74 (m, 2H). |

-continued

| Example | Structure | Name | Method | NMR |
|---|---|---|---|---|
| 9 | 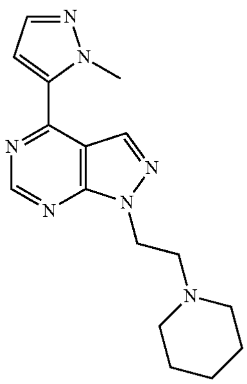 [SMILES: Cn1nccc1-c1ncnc2c1cnn2CCN1CCCCC1] | 4-(1-methyl-1H-pyrazol-5-yl)-1-(2-(piperidin-1-yl)ethyl)-1H-pyrazolo[3,4-d]pyrimidine | A | ¹H NMR (CDCl₃) δ: 9.03 (s, 1H), 8.24 (s, 1H), 7.64 (d, J = 1.1 Hz, 1H), 7.01 (d, J = 1.1 Hz, 1H), 4.66 (t, J = 7.0 Hz, 2H), 4.37 (s, 3H), 2.90 (t, J = 6.0 Hz, 2H), 2.65-2.29 (m, 4H), 1.61-1.44 (m, 4H), 1.44-1.32 (m, 2H). |
| 10 | 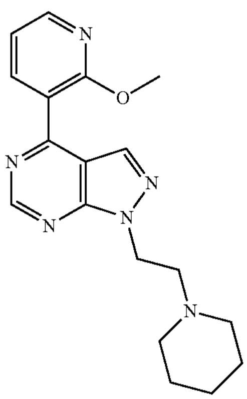 [SMILES: COc1ncccc1-c1ncnc2c1cnn2CCN1CCCCC1] | 4-(2-methoxypyridin-3-yl)-1-(2-(piperidin-1-yl)ethyl)-1H-pyrazolo[3,4-d]pyrimidine | A | ¹H NMR (CDCl₃) δ: 9.06 (s, 1H), 8.43-8.28 (m, 1H), 8.19 (dd, J = 7.7, 2.1 Hz, 1H), 8.14 (s, 1H), 7.11 (dd, J = 7.5, 5.0 Hz, 1H), 4.66 (t, J = 7.2 Hz, 2H), 4.04 (s, 3H), 2.91 (t, J = 7.3 Hz, 2H), 2.72-2.33 (m, 4H), 1.79-1.46 (m, 4H), 1.46-1.29 (m, 2H). |
| 11 | | 4-(2-methoxypyridin-3-yl)-1-(2-(piperidin-1-yl)ethyl)-1H-pyrazolo[3,4-d]pyrimidine (L)-tartrate | C | ¹H NMR (DMSO) δ: 9.07 (s, 1H), 8.42 (d, J = 4.6 Hz, 1H), 8.29 (s, 1H), 8.21 (d, J = 7.4 Hz, 1H), 7.33-7.10 (m, 1H), 4.64 (t, J = 6.6 Hz, 2H), 4.23 (s, 2H), 4.00 (s, 3H), 2.99 (t, J = 6.6 Hz, 2H), 2.59 (t, J = 5.2 Hz, 4H), 1.59-1.43 (m, 4H), 1.43-1.28 (m, 2H). |
| 12 | 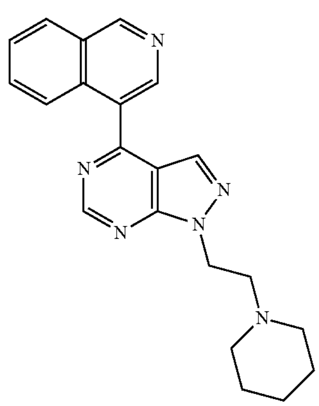 [SMILES: c1ccc2c(-c3ncnc4c3cnn4CCN3CCCCC3)cncc2c1] | 4-(1-(2-(piperidin-1-yl)ethyl)-1H-pyrazolo[3,4-d]pyrimidin-4-yl)isoquinoline | A | ¹H NMR (CDCl₃) δ: 9.42 (s, 1H), 9.20 (s, 1H), 8.90 (s, 1H), 8.40 (d, J = 8.2 Hz, 1H), 8.14 (d, J = 2.8 Hz, 1H), 8.12 (s, 1H), 7.76 (dt, J = 16.4, 7.1 Hz, 2H), 4.72 (t, J = 7.2 Hz, 2H), 2.95 (t, J = 7.1 Hz, 2H), 2.60-2.41 (m, 4H), 1.62-1.49 (m, 4H), 1.49-1.35 (m, 2H). |

-continued

| Example | Structure | Name | Method | NMR |
|---|---|---|---|---|
| 13 | 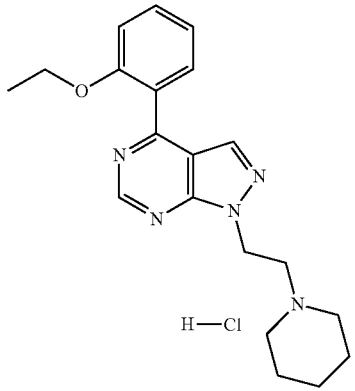 | 4-(2-ethoxyphenyl)-1-(2-(piperidin-1-yl)ethyl)-1H-pyrazolo[3,4-d]pyrimidine hydrochloride | A then C | $^1$H NMR (CDCl$_3$) δ: 12.69 (s, 1H), 9.19 (s, 1H), 8.28 (s, 1H), 7.94-7.77 (m, 1H), 7.57 (t, J = 7.9 Hz, 1H), 7.24-7.11 (m, 1H), 7.10 (d, J = 8.3 Hz, 1H), 5.28-5.03 (m, 2H), 4.18 (q, J = 7.0 Hz, 2H), 3.80-3.46 (m, 4H), 2.98-2.54 (m, 2H), 2.00-1.71 (m, 4H), 1.50-1.10 (m, 2H), 1.33 (t, J = 6.7 Hz, 3H). |
| 14 | 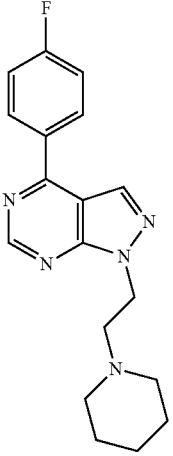 [SMILES: Fc1ccc(-c2ncnc3c2cnn3CCN2CCCCC2)cc1] | 4-(4-fluorophenyl)-1-(2-(piperidin-1-yl)ethyl)-1H-pyrazolo[3,4-d]pyrimidine | A | $^1$H NMR (CDCl$_3$) δ: 9.04 (s, 1H), 8.33 (s, 1H), 8.23 (dd, J = 8.9, 5.3 Hz, 2H), 7.35-7.22 (m, 2H), 4.74 (t, J = 6.9 Hz, 2H), 3.12-2.92 (m, 2H), 2.70-2.47 (m, 4H), 1.66-1.54 (m, 4H), 1.49-1.38 (m, 2H). |
| 15 | 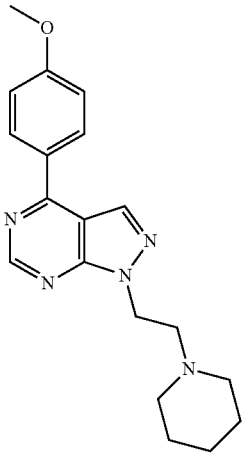 [SMILES: COc1ccc(-c2ncnc3c2cnn3CCN2CCCCC2)cc1] | 4-(4-methoxyphenyl)-1-(2-(piperidin-1-yl)ethyl)-1H-pyrazolo[3,4-d]pyrimidine | A | $^1$H NMR (CDCl$_3$) δ: 9.00 (s, 1H), 8.35 (s, 1H), 8.21 (d, J = 8.9 Hz, 2H), 7.10 (d, J = 8.9 Hz, 2H), 4.71 (t, J = 7.0 Hz, 2H), 3.92 (s, 3H), 3.00 (t, J = 6.8 Hz, 2H), 2.67-2.47 (m, 4H), 1.65-1.51 (m, 4H), 1.49-1.36 (m, 2H). |

-continued

| Example | Structure | Name | Method | NMR |
|---|---|---|---|---|
| 16 | 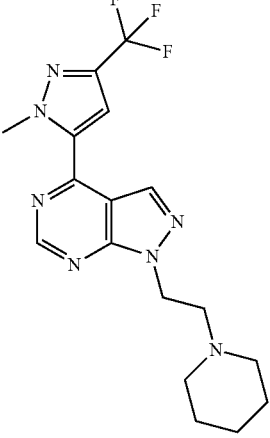 | 4-(1-methyl-3-(trifluoromethyl)-1H-pyrazol-5-yl)-1-(2-(piperidin-1-yl)ethyl)-1H-pyrazolo[3,4-d]pyrimidine | A | $^1$H NMR (CDCl$_3$) δ: 9.07 (s, 1H), 8.25 (s, 1H), 7.22 (s, 1H), 4.73 (t, J = 5.9 Hz, 2H), 4.42 (s, 3H), 3.09-2.86 (m, 2H), 2.68-2.40 (m, 4H), 1.67-1.48 (m, 4H), 1.48-1.34 (m, 2H). |
| 17 | 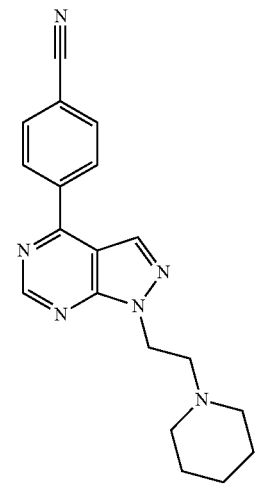 [SMILES: N#Cc1ccc(-c2ncnc3c2cnn3CCN2CCCCC2)cc1] | 4-(1-(2-(piperidin-1-yl)ethyl)-1H-pyrazolo[3,4-d]pyrimidin-4-yl)benzonitrile | A | $^1$H NMR (CDCl$_3$) δ: 9.10 (s, 1H), 8.34 (s, 1H), 8.32 (d, J = 8.4 Hz, 2H), 7.89 (d, J = 8.4 Hz, 2H), 4.76 (t, J = 7.0 Hz, 2H), 3.23-2.87 (m, 2H), 2.77-2.40 (m, 4H), 1.73-1.48 (m, 4H), 1.50-1.29 (m, 2H). |
| 18 | 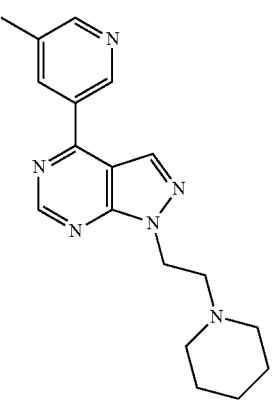 [SMILES: Cc1cncc(-c2ncnc3c2cnn3CCN2CCCCC2)c1] | 4-(5-methylpyridin-3-yl)-1-(2-(piperidin-1-yl)ethyl)-1H-pyrazolo[3,4-d]pyrimidine | A | $^1$H NMR (CDCl$_3$) δ: 9.21 (d, J = 1.9 Hz, 1H), 9.08 (s, 1H), 8.64 (d, J = 2.1 Hz, 1H), 8.37 (s, 1H), 8.33 (t, J = 2.1 Hz, 1H), 4.68 (t, J = 7.1 Hz, 2H), 2.91 (t, J = 7.1 Hz, 2H), 2.57-2.42 (m, 4H), 2.49 (s, 3H), 1.65-1.45 (m, 4H), 1.45-1.33 (m, 2H). |

-continued

| Example | Structure | Name | Method | NMR |
|---|---|---|---|---|
| 19 | 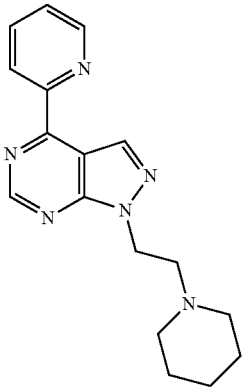 [SMILES: c1ccc(-c2ncnc3c2cnn3CCN2CCCCC2)nc1] | 1-(2-(piperidin-1-yl)ethyl)-4-(pyridin-2-yl)-1H-pyrazolo[3,4-d]pyrimidine | B | $^1$H NMR (CDCl$_3$) δ: 9.07 (s, 1H), 8.95 (s, 1H), 8.90-8.81 (m, 1H), 8.63 (d, J = 7.9 Hz, 1H), 7.99-7.82 (m, 1H), 7.54-7.39 (m, 2H), 4.68 (t, J = 7.1 Hz, 2H), 2.92 (t, J = 7.1 Hz, 2H), 2.66-2.35 (m, 4H), 1.60-1.46 (m, 4H), 1.46-1.31 (m, 2H). |
| 20 | 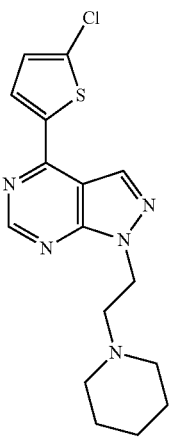 [SMILES: Clc1ccc(-c2ncnc3c2cnn3CCN2CCCCC2)s1] | 4-(5-chlorothiophen-2-yl)-1-(2-(piperidin-1-yl)ethyl)-1H-pyrazolo[3,4-d]pyrimidine | A | $^1$H NMR (CD$_3$OD) δ: 8.82 (s, 1H), 8.61 (s, 1H), 8.10 (d, J = 4.1 Hz, 1H), 7.21 (d, J = 4.0 Hz, 1H), 4.67 (t, J = 6.7 Hz, 2H), 2.92 (t, J = 6.7 Hz, 2H), 2.61-2.43 (m, 4H), 1.60-1.47 (m, 4H), 1.47-1.35 (m, 2H) |
| 21 | 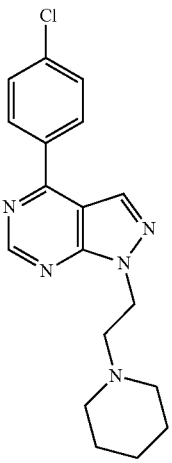 | 4-(4-chlorophenyl)-1-(2-(piperidin-1-yl)ethyl)-1H-pyrazolo[3,4-d]pyrimidine | A | $^1$H NMR (CDCl$_3$) δ: 9.05 (s, 1H), 8.33 (s, 1H), 8.16 (d, J = 8.7 Hz, 2H), 7.58 (d, J = 8.6 Hz, 2H), 4.90-4.54 (m, 2H), 3.22-2.84 (m, 2H), 2.74-2.41 (m, 4H), 1.76-1.49 (m, 4H), 1.49-1.31 (m, 2H). |

| Example | Structure | Name | Method | NMR |
|---|---|---|---|---|
| 22 | 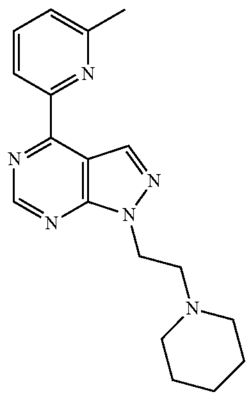 [SMILES: Cc1cccc(-c2ncnc3c2cnn3CCN2CCCCC2)n1] | 4-(6-methylpyridin-2-yl)-1-(2-(piperidin-1-yl)ethyl)-1H-pyrazolo[3,4-d]pyrimidine | B | $^1$H NMR (CDCl$_3$) δ: 9.05 (s, 1H), 8.98 (s, 1H), 8.41 (d, J = 7.6 Hz, 1H), 7.87-7.70 (m, 1H), 7.31 (d, J = 8.1 Hz, 1H), 4.67 (t, J = 7.0 Hz, 2H), 2.91 (t, J = 6.8 Hz, 2H), 2.72 (s, 3H), 2.56-2.41 (m, 4H), 1.61-1.45 (m, 4H), 1.45-1.32 (m, 2H). |
| 23 | 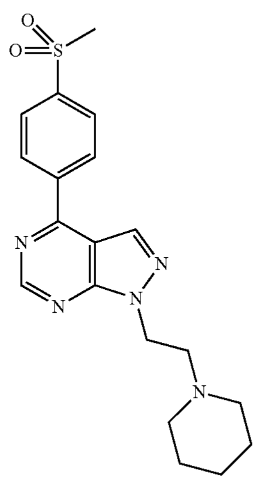 [SMILES: CS(=O)(=O)c1ccc(-c2ncnc3c2cnn3CCN2CCCCC2)cc1] | 4-(4-(methylsulfonyl)phenyl)-1-(2-(piperidin-1-yl)ethyl)-1H-pyrazolo[3,4-d]pyrimidine | A | $^1$H NMR (CD$_3$OD) δ: 9.09 (s, 1H), 8.61 (s, 1H), 8.51 (d, J = 8.7 Hz, 2H), 8.21 (d, J = 8.6 Hz, 2H), 4.74 (t, J = 6.7 Hz, 2H), 3.22 (s, 3H), 2.98 (t, J = 6.8 Hz, 2H), 2.57 (t, J = 5.2 Hz, 4H), 1.67-1.50 (m, 4H), 1.50-1.37 (m, 2H). |
| 24 | 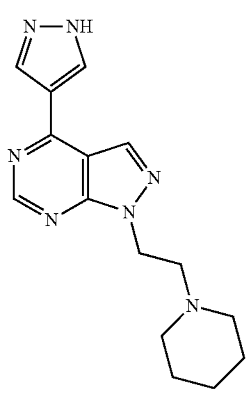 [SMILES: c1nc(-c2cn[nH]c2)c2cnn(CCN3CCCCC3)c2n1] | 1-(2-(piperidin-1-yl)ethyl)-4-(1H-pyrazol-4-yl)-1H-pyrazolo[3,4-d]pyrimidine | A | $^1$H NMR (CD$_3$OD) δ: 8.81 (dd, J = 2.8, 0.7 Hz, 1H), 8.77 (s, 1H), 8.68 (s, 1H), 7.99 (dd, J = 1.6, 0.7 Hz, 1H), 6.65 (dd, J = 2.8, 1.6 Hz, 1H), 4.67 (t, J = 6.8 Hz, 2H), 2.92 (t, J = 6.8 Hz, 2H), 2.53 (t, J = 5.3 Hz, 4H), 1.64-1.48 (m, 4H), 1.48-1.34 (m, 2H). |

-continued

| Example | Structure | Name | Method | NMR |
|---|---|---|---|---|
| 25 | 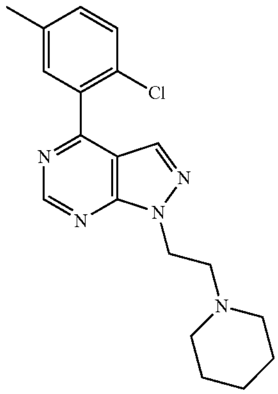 [SMILES: Cc1ccc(Cl)c(-c2ncnc3c2cnn3CCN2CCCCC2)c1] | 4-(2-chloro-5-methylphenyl)-1-(2-(piperidin-1-yl)ethyl)-1H-pyrazolo[3,4-d]pyrimidine | A | $^1$H NMR (CDCl$_3$) δ: 9.10 (s, 1H), 8.06 (s, 1H), 7.45 (d, J = 8.3 Hz, 1H), 7.43 (d, J = 2.0 Hz, 1H), 7.28 (dd, J = 8.1, 2.1 Hz, 1H), 4.73 (t, J = 7.3 Hz, 2H), 3.11-2.92 (m, 2H), 2.70-2.48 (m, 4H), 2.41 (s, 3H), 1.72-1.51 (m, 4H), 1.51-1.36 (m, 2H). |
| 26 | 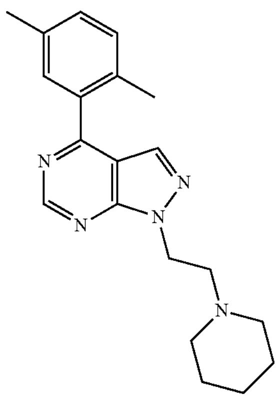 [SMILES: Cc1ccc(C)c(-c2ncnc3c2cnn3CCN2CCCCC2)c1] | 4-(2,5-dimethylphenyl)-1-(2-(piperidin-1-yl)ethyl)-1H-pyrazolo[3,4-d]pyrimidine | A | $^1$H NMR (CD$_3$OD) δ: 9.00 (s, 1H), 8.10 (s, 1H), 7.39-7.26 (m, 3H), 4.71 (t, J = 6.7 Hz, 2H), 2.96 (t, J = 6.7 Hz, 2H), 2.57 (t, J = 5.1 Hz, 4H), 2.40 (s, 3H), 2.31 (s, 3H), 1.64-1.50 (m, 4H), 1.50-1.37 (m, 2H). |
| 27 | 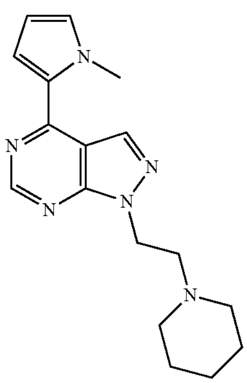 [SMILES: Cn1cccc1-c1ncnc2c1cnn2CCN1CCCCC1] | 4-(1-methyl-1H-pyrrol-2-yl)-1-(2-(piperidin-1-yl)ethyl)-1H-pyrazolo[3,4-d]pyrimidine | A | $^1$H NMR (CDCl$_3$) δ: 8.88 (s, 1H), 8.26 (s, 1H), 7.11 (dd, J = 4.0, 1.7 Hz, 1H), 6.92 (t, J = 2.1 Hz, 1H), 6.32 (dd, J = 4.0, 2.6 Hz, 1H), 4.89-4.55 (m, 2H), 4.16 (s, 3H), 3.22-2.90 (m, 2H), 2.78-2.40 (m, 4H), 1.79-1.53 (m, 4H), 1.53-1.33 (m, 2H). |
| 28 | 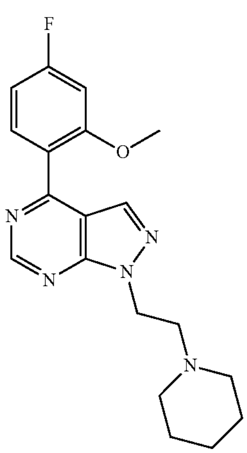 [SMILES: COc1cc(F)ccc1-c1ncnc2c1cnn2CCN1CCCCC1] | 4-(4-fluoro-2-methoxyphenyl)-1-(2-(piperidin-1-yl)ethyl)-1H-pyrazolo[3,4-d]pyrimidine | A | $^1$H NMR (CDCl$_3$) δ: 9.05 (s, 1H), 8.05 (s, 1H), 7.81 (dd, J = 8.6, 6.8 Hz, 1H), 6.90-6.73 (m, 2H), 4.83-4.61 (m, 2H), 3.88 (s, 3H), 3.18-2.89 (m, 2H), 2.72-2.35 (m, 4H), 1.76-1.54 (m, 4H), 1.55-1.30 (m, 2H). |

-continued

| Example | Structure | Name | Method | NMR |
|---|---|---|---|---|
| 29 | 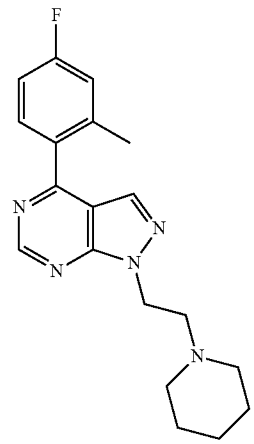 [SMILES: Cc1cc(F)ccc1-c1ncnc2c1cnn2CCN1CCCCC1] | 4-(4-fluoro-2-methylphenyl)-1-(2-(piperidin-1-yl)ethyl)-1H-pyrazolo[3,4-d]pyrimidine | A | $^1$H NMR (CDCl$_3$) δ: 9.06 (s, 1H), 8.00 (s, 1H), 7.77-7.60 (m, 1H), 7.53 (dd, J = 8.3, 5.9 Hz, 1H), 7.16-6.99 (m, 1H), 4.97-4.59 (m, 2H), 3.25-2.87 (m, 2H), 2.76-2.50 (m, 4H), 2.45 (s, 3H), 1.81-1.54 (m, 4H), 1.54-1.36 (m, 2H). |
| 30 | 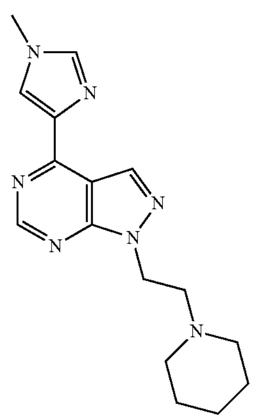 [SMILES: Cn1cnc(-c2ncnc3c2cnn3CCN2CCCCC2)c1] | 4-(1-methyl-1H-imidazol-4-yl)-1-(2-(piperidin-1-yl)ethyl)-1H-pyrazolo[3,4-d]pyrimidine | A | $^1$H NMR (CD$_3$OD) δ: 8.82 (s, 1H), 8.75 (s, 1H), 8.11 (s, 1H), 7.85 (s, 1H), 4.66 (t, J = 6.8 Hz, 2H), 3.87 (s, 3H), 2.94 (t, J = 6.8 Hz, 2H), 2.63-2.45 (m, 4H), 1.65-1.49 (m, 4H), 1.49-1.34 (m, 2H). |
| 31 | 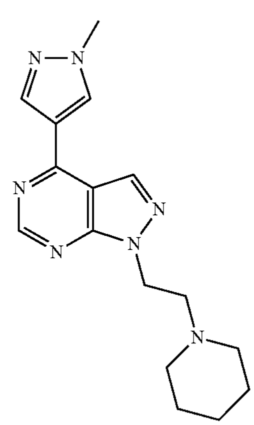 [SMILES: Cn1cc(-c2ncnc3c2cnn3CCN2CCCCC2)cn1] | 4-(1-methyl-1H-pyrazol-4-yl)-1-(2-(piperidin-1-yl)ethyl)-1H-pyrazolo[3,4-d]pyrimidine | A | $^1$H NMR (CD$_3$OD) δ: 8.83 (s, 1H), 8.63 (s, 1H), 8.58 (s, 1H), 8.37 (s, 1H), 4.65 (t, J = 6.8 Hz, 2H), 4.03 (s, 3H), 2.91 (t, J = 6.8 Hz, 2H), 2.61-2.40 (m, 4H), 1.62-1.48 (m, 4H), 1.48-1.37 (m, 2H). |

| Example | Structure | Name | Method | NMR |
|---|---|---|---|---|
| 32 | 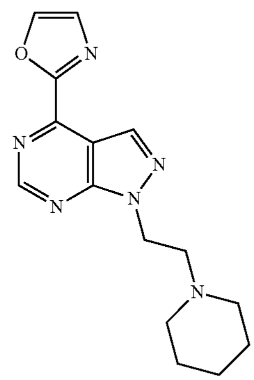 [SMILES: c1coc(-c2ncnc3c2cnn3CCN2CCCCC2)n1] | 2-(1-(2-(piperidin-1-yl)ethyl)-1H-pyrazolo[3,4-d]pyrimidin-4-yl)oxazole | A | ¹H NMR (CDCl₃) δ: 9.12 (s, 1H), 8.71 (s, 1H), 7.98 (d, J = 0.7 Hz, 1H), 7.53 (d, J = 0.7 Hz, 1H), 5.07-4.56 (m, 2H), 3.52-2.79 (m, 2H), 2.84-2.33 (m, 4H), 1.91-1.53 (m, 4H), 1.53-1.20 (m, 2H). |
| 33 | 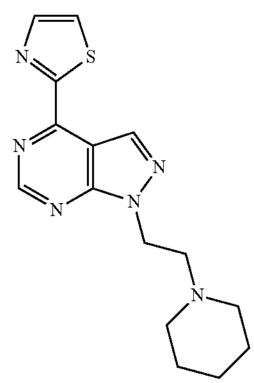 [SMILES: c1csc(-c2ncnc3c2cnn3CCN2CCCCC2)n1] | 2-(1-(2-(piperidin-1-yl)ethyl)-1H-pyrazolo[3,4-d]pyrimidin-4-yl)thiazole | B | ¹H NMR (CDCl₃) δ: 9.01 (s, 1H), 8.81 (s, 1H), 8.16 (d, J = 3.1 Hz, 1H), 7.65 (d, J = 3.1 Hz, 1H), 4.76 (t, J = 5.5 Hz, 2H), 3.26-2.90 (m, 2H), 2.85-2.39 (m, 4H), 1.78-1.50 (m, 4H), 1.50-1.35 (m, 2H). |
| 34 | 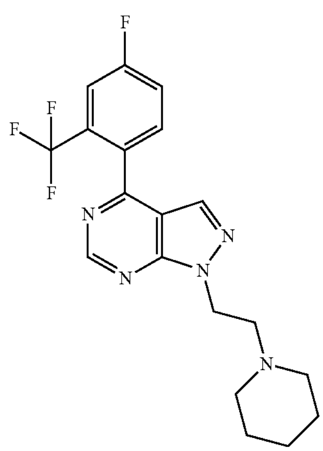 [SMILES: Fc1ccc(-c2ncnc3c2cnn3CCN2CCCCC2)c(C(F)(F)F)c1] | 4-(4-fluoro-2-(trifluoromethyl)phenyl)-1-(2-(piperidin-1-yl)ethyl)-1H-pyrazolo[3,4-d]pyrimidine | A | ¹H NMR (CDCl₃) δ: 9.07 (s, 1H), 7.92 (s, 1H), 7.66-7.52 (m, 2H), 7.42 (td, J = 8.0, 2.6 Hz, 1H), 5.02-4.59 (m, 2H), 3.27-2.89 (m, 2H), 2.76-2.31 (m, 4H), 1.93-1.53 (m, 4H), 1.53-1.36 (m, 2H). |
| 35 | 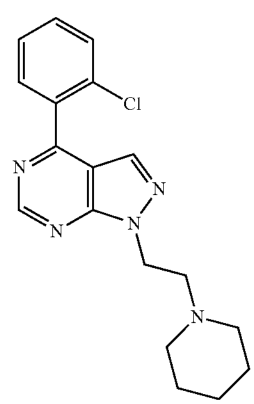 [SMILES: Clc1ccccc1-c1ncnc2c1cnn2CCN1CCCCC1] | 4-(2-chlorophenyl)-1-(2-(piperidin-1-yl)ethyl)-1H-pyrazolo[3,4-d]pyrimidine | A | ¹H NMR (CDCl₃) δ: 9.11 (s, 1H), 8.06 (s, 1H), 7.73-7.40 (m, 4H), 4.97-4.60 (m, 2H), 3.29-2.86 (m, 2H), 2.86-2.42 (m, 2H), 1.87-1.51 (m, 4H), 1.51-1.36 (m, 2H). |

| Example | Structure | Name | Method | NMR |
|---|---|---|---|---|
| 36 | 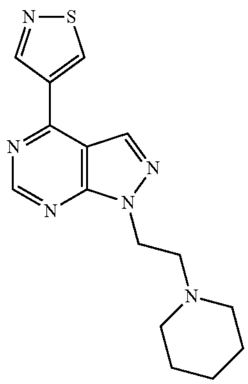 [SMILES: c1nc(-c2cnsc2)c2cnn(CCN3CCCCC3)c2n1] | 4-(1-(2-(piperidin-1-yl)ethyl)-1H-pyrazolo[3,4-d]pyrimidin-4-yl)isothiazole | A | $^1$H NMR (CDCl$_3$) δ: 9.53 (s, 1H), 9.33 (s, 1H), 9.04 (s, 1H), 8.35 (s, 1H), 5.11-4.57 (m, 2H), 3.29-2.85 (m, 2H), 2.86-2.42 (m, 4H), 1.86-1.51 (m, 4H), 1.52-1.36 (m, 2H). |
| 37 | 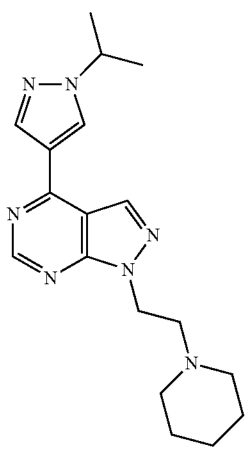 [SMILES: CC(C)n1cc(-c2ncnc3c2cnn3CCN2CCCCC2)cn1] | 4-(1-isopropyl-1H-pyrazol-4-yl)-1-(2-(piperidin-1-yl)ethyl)-1H-pyrazolo[3,4-d]pyrimidine | A | $^1$H NMR (CD$_3$OD) δ: 8.82 (s, 1H), 8.65 (s, 1H), 8.61 (s, 1H), 8.40 (s, 1H), 4.78-4.67 (m, 1H), 4.65 (t, J = 6.9 Hz, 2H), 2.92 (t, J = 6.8 Hz, 2H), 2.53 (t, J = 5.2 Hz, 4H), 1.59 (d, J = 6.7 Hz, 6H), 1.57-1.49 (m, 4H), 1.49-1.33 (m, 2H). |
| 38 | 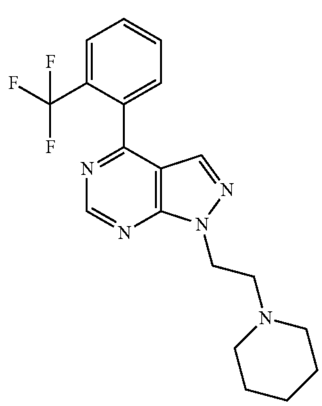 [SMILES: FC(F)(F)c1ccccc1-c1ncnc2c1cnn2CCN1CCCCC1] | 1-(2-(piperidin-1-yl)ethyl)-4-(2-(trifluoromethyl)phenyl)-1H-pyrazolo[3,4-d]pyrimidine | A | $^1$H NMR (CD$_3$OD) δ: 9.02 (s, 1H), 8.03 (s, 1H), 7.95 (dd, J = 7.6, 1.5 Hz, 1H), 7.88-7.74 (m, 2H), 7.65 (dd, J = 7.5, 1.6 Hz, 1H), 4.72 (t, J = 6.7 Hz, 2H), 2.94 (t, J = 6.7 Hz, 2H), 2.54 (t, J = 5.2 Hz, 4H), 1.61-1.48 (m, 4H), 1.48-1.36 (m, 2H). |

-continued

| Example | Structure | Name | Method | NMR |
|---|---|---|---|---|
| 39 | 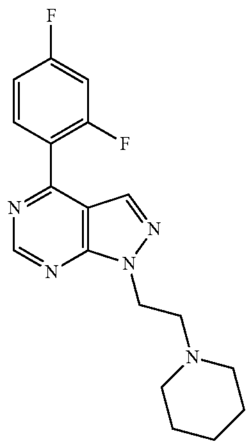 [SMILES: Fc1ccc(-c2ncnc3c2cnn3CCN2CCCCC2)c(F)c1] | 4-(2,4-difluorophenyl)-1-(2-(piperidin-1-yl)ethyl)-1H-pyrazolo[3,4-d]pyrimidine | A | $^1$H NMR (CD$_3$OD) δ: 9.04 (s, 1H), 8.27 (s, 1H), 8.12-7.95 (m, 1H), 7.33-7.12 (m, 2H), 4.71 (t, J = 6.9 Hz, 2H), 2.95 (t, J = 6.7 Hz, 2H), 2.71-2.46 (m, 4H), 1.62-1.49 (m, 4H), 1.49-1.37 (m, 2H). |
| 40 | 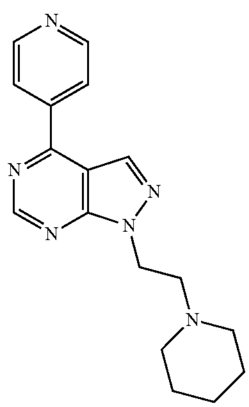 [SMILES: c1cc(-c2ncnc3c2cnn3CCN2CCCCC2)ccn1] | 1-(2-(piperidin-1-yl)ethyl)-4-(pyridin-4-yl)-1H-pyrazolo[3,4-d]pyrimidine | B | $^1$H NMR (CD$_3$OD) δ: 9.11 (s, 1H), 8.83 (d, J = 6.3 Hz, 2H), 8.65 (s, 1H), 8.26 (d, J = 6.3 Hz, 2H), 4.73 (t, J = 6.7 Hz, 2H), 2.95 (t, J = 6.7 Hz, 2H), 2.54 (t, J = 5.2 Hz, 4H), 1.62-1.49 (m, 4H), 1.49-1.35 (m, 2H). |
| 41 | 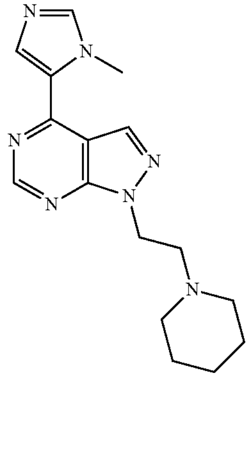 [SMILES: Cn1cncc1-c1ncnc2c1cnn2CCN1CCCCC1] | 4-(1-methyl-1H-imidazol-5-yl)-1-(2-(piperidin-1-yl)ethyl)-1H-pyrazolo[3,4-d]pyrimidine | A | $^1$H NMR (CD$_3$OD) δ: 8.95 (s, 1H), 8.49 (s, 1H), 8.07 (d, J = 0.9 Hz, 1H), 7.94 (s, 1H), 4.67 (t, J = 6.8 Hz, 2H), 4.19 (s, 3H), 2.92 (t, J = 6.8 Hz, 2H), 2.53 (t, J = 4.8 Hz, 4H), 1.62-1.48 (m, 4H), 1.49-1.38 (m, 2H). |

| Example | Structure | Name | Method | NMR |
|---|---|---|---|---|
| 42 | 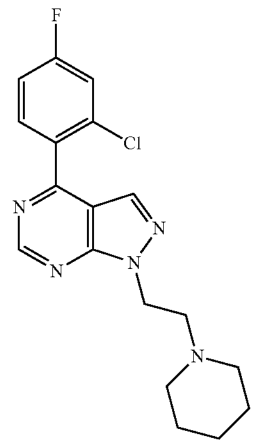 [SMILES: Fc1ccc(-c2ncnc3c2cnn3CCN2CCCCC2)c(Cl)c1] | 4-(2-chloro-4-fluorophenyl)-1-(2-(piperidin-1-yl)ethyl)-1H-pyrazolo[3,4-d]pyrimidine | A | $^1$H NMR (CD$_3$OD) δ: 9.05 (s, 1H), 8.16 (s, 1H), 7.72 (dd, J = 8.5, 6.1 Hz, 1H), 7.51 (dd, J = 8.7, 2.3 Hz, 1H), 7.34 (td, J = 8.4, 2.3 Hz, 1H), 4.71 (t, J = 6.7 Hz, 2H), 2.94 (t, J = 6.7 Hz, 2H), 2.60-2.47 (m, 4H), 1.62-1.48 (m, 4H), 1.49-1.36 (m, 2H). |
| 43 | 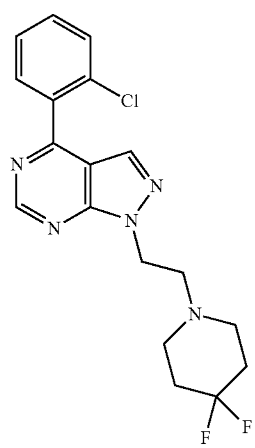 [SMILES: FC1(F)CCN(CCn2ncc3c(-c4ccccc4Cl)ncnc32)CC1] | 4-(2-chlorophenyl)-1-(2-(4,4-difluoropiperidin-1-yl)ethyl)-1H-pyrazolo[3,4-d]pyrimidine | A | $^1$H NMR (CDCl$_3$) δ: 9.10 (s, 1H), 8.06 (s, 1H), 7.68-7.54 (m, 2H), 7.54-7.40 (m, 2H), 4.67 (t, J = 5.8 Hz, 2H), 3.01 (t, J = 6.5 Hz, 2H), 2.75-2.59 (m, 4H), 2.02-1.75 (m, 4H). |
| 44 | 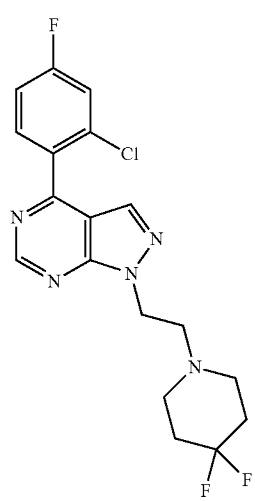 [SMILES: Fc1ccc(-c2ncnc3c2cnn3CCN2CCC(F)(F)CC2)c(Cl)c1] | 4-(2-chloro-4-fluorophenyl)-1-(2-(4,4-difluoropiperidin-1-yl)ethyl)-1H-pyrazolo[3,4-d]pyrimidine | A | $^1$H NMR (CD$_3$OD) δ: 9.06 (s, 1H), 8.17 (s, 1H), 7.72 (dd, J = 8.6, 6.0 Hz, 1H), 7.51 (dd, J = 8.7, 2.5 Hz, 1H), 7.34 (td, J = 8.4, 2.5 Hz, 1H), 4.71 (t, J = 6.3 Hz, 2H), 3.01 (t, J = 6.3 Hz, 2H), 2.66 (t, J = 5.5 Hz, 4H), 1.94-1.73 (m, 4H). |

| Example | Structure | Name | Method | NMR |
|---------|-----------|------|--------|-----|
| 45 | 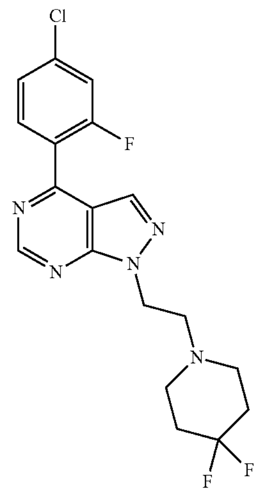 [SMILES: Fc1cc(Cl)ccc1-c1ncnc2c1cnn2CCN1CCC(F)(F)CC1] | 4-(4-chloro-2-fluorophenyl)-1-(2-(4,4-difluoropiperidin-1-yl)ethyl)-1H-pyrazolo[3,4-d]pyrimidine | A | $^1$H NMR (CD$_3$OD) δ: 9.05 (s, 1H), 8.28 (d, J = 4.2 Hz, 1H), 7.99 (t, J = 8.1 Hz, 1H), 7.60-7.39 (m, 2H), 4.70 (t, J = 6.3 Hz, 2H), 3.00 (t, J = 6.3 Hz, 2H), 2.66 (t, J = 5.8 Hz, 4H), 1.94-1.71 (m, 4H). |
| 46 | 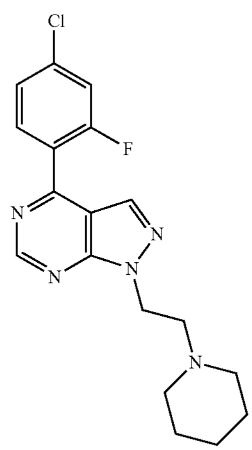 [SMILES: Fc1cc(Cl)ccc1-c1ncnc2c1cnn2CCN1CCCCC1] | 4-(4-chloro-2-fluorophenyl)-1-(2-(piperidin-1-yl)ethyl)-1H-pyrazolo[3,4-d]pyrimidine | A | $^1$H NMR (CD$_3$OD) δ: 9.05 (s, 1H), 8.27 (d, J = 4.1 Hz, 1H), 7.98 (t, J = 8.1 Hz, 1H), 7.57-7.42 (m, 2H), 4.70 (t, J = 6.7 Hz, 2H), 2.93 (t, J = 6.7 Hz, 2H), 2.61-2.45 (m, 4H), 1.60-1.48 (m, 4H), 1.48-1.35 (m, 2H). |
| 47 | 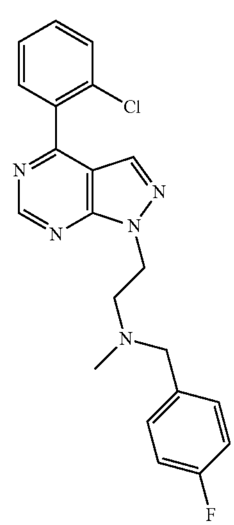 [SMILES: CN(CCn1ncc2c(-c3ccccc3Cl)ncnc21)Cc1ccc(F)cc1] | 2-(4-(2-chlorophenyl)-1H-pyrazolo[3,4-d]pyrimidin-1-yl)-N-(4-fluorobenzyl)-N-methylethanamine | A | $^1$H NMR (CD$_3$OD) δ: 8.98 (s, 1H), 8.11 (s, 1H), 7.73-7.50 (m, 4H), 6.97 (dd, J = 8.4, 5.6 Hz, 2H), 6.84 (t, J = 8.7 Hz, 2H), 4.69 (t, J = 6.1 Hz, 2H), 3.49 (s, 2H), 2.96 (t, J = 6.1 Hz, 2H), 2.30 (s, 3H). |

-continued

| Example | Structure | Name | Method | NMR |
|---|---|---|---|---|
| 48 | 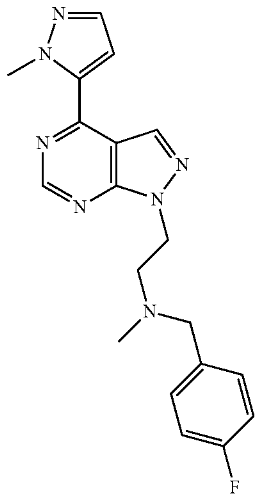 [SMILES: CN(CCn1ncc2c(-c3ccnn3C)ncnc21)Cc1ccc(F)cc1] | N-(4-fluorobenzyl)-N-methyl-2-(4-(1-methyl-1H-pyrazol-5-yl)-1H-pyrazolo[3,4-d]pyrimidin-1-yl)ethanamine | A | $^1$H NMR (CDCl$_3$) δ: 9.00 (s, 1H), 8.23 (s, 1H), 7.66 (d, J = 2.1 Hz, 1H), 7.02 (d, J = 2.1 Hz, 1H), 7.00 (s, 2H), 6.85 (t, J = 8.5 Hz, 2H), 4.66 (t, J = 6.3 Hz, 2H), 4.40 (s, 3H), 3.51 (s, 2H), 2.98 (t, J = 6.3 Hz, 2H), 2.30 (s, 3H). |
| 49 | 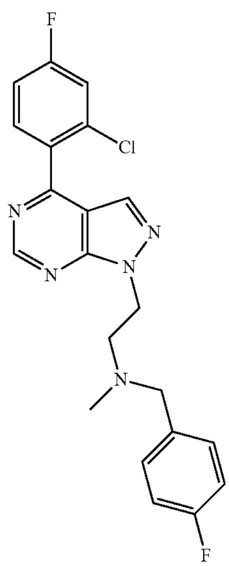 [SMILES: CN(CCn1ncc2c(-c3ccc(F)cc3Cl)ncnc21)Cc1ccc(F)cc1] | 2-(4-(2-chloro-4-fluorophenyl)-1H-pyrazolo[3,4-d]pyrimidin-1-yl)-N-(4-fluorobenzyl)-N-methylethanamine | A | $^1$H NMR (CDCl$_3$) δ: 9.05 (s, 1H), 8.05 (s, 1H), 7.65 (dd, J = 8.6, 6.0 Hz, 1H), 7.35 (dd, J = 8.4, 2.5 Hz, 1H), 7.20 (ddd, J = 8.6, 7.8, 2.5 Hz, 1H), 7.00 (dd, J = 8.3, 5.6 Hz, 2H), 6.85 (t, J = 8.7 Hz, 2H), 4.67 (t, J = 6.3 Hz, 2H), 3.51 (s, 2H), 2.99 (t, J = 6.3 Hz, 2H), 2.31 (s, 3H). |

Pharmacological Study

Brain membrane preparation and binding assays for the σ1-receptor were performed as described (DeHaven-Hudkins, D. L., L. C. Fleissner, and F. Y. Ford-Rice, 1992, Characterization of the binding of [$^3$H](+)pentazocine to α recognition sites in guinea pig brain, Eur. J. Pharmacol. 227, 371-378) with some modifications. Guinea pig brains were homogenized in 10 vols. (w/v) of Tris-HCl 50 mM 0.32 M sucrose, pH 7.4, with a Kinematica Polytron PT 3000 at 15000 r.p.m. for 30 s. The homogenate was centrifuged at 1000 g for 10 min at 4° C. and the supernatants collected and centrifuged again at 48000 g for 15 min at 4° C. The pellet was resuspended in 10 volumes of Tris-HCl buffer (50 mM, pH 7.4), incubated at 37° C. for 30 min, and centrifuged at 48000 g for 20 min at 4° C. Following this, the pellet was resuspended in fresh Tris-HCl buffer (50 mM, pH 7.4) and stored on ice until use.

The radioligand used was [$^3$H]-(+)-pentazocine at 5.0 nM and the final volume was 200 μl. The incubation was initiated with the addition of 100 μl of membrane at a final tissue concentration of approximately 5 mg tissue net weight/mL and the incubation time was 150 m. at 37° C. After incubation, the membranes were collected onto pretreated glass fiber filterplate (MultiScreen-FC, Millipore), with polyethylenimine 0.1%. The filters were washed two times with 200 μl of washing buffer (50 mM Tris Cl, pH=7.4) and then 25 μl of Ecoscint H liquid scintillation cocktail were added. Microplates were allowed to set for several hours and then quantified by liquid scintillation spectrophotometry (1450 Microbeta, Wallac). Nonspecific binding was determined with 1 μM haloperidol.

Pharmacological Results

| Ex. | Ki (nM) |
|---|---|
| 1 | 99.6 |
| 2 | 73.8 |
| 3 | 82.5 |
| 6 | 72.4 |

-continued

| Ex. | Ki (nM) |
|---|---|
| 9 | 40.6 |
| 10 | 112.1 |
| 11 | 151 |
| 13 | 299.8 |
| 14 | 95.4 |
| 16 | 137.4 |
| 18 | 447.3 |
| 20 | 35 |
| 21 | 42.6 |
| 25 | 31.2 |
| 26 | 55.4 |
| 27 | 31.5 |
| 28 | 39.2 |
| 29 | 48.4 |
| 34 | 57 |
| 35 | 75.7 |
| 36 | 475.2 |
| 38 | 125.3 |
| 39 | 81.6 |
| 42 | 27 |
| 44 | 318.4 |
| 46 | 111.6 |
| 47 | 76.6 |
| 48 | 34.1 |
| 49 | 61.7 |

The invention claimed is:

1. A compound of general formula (I):

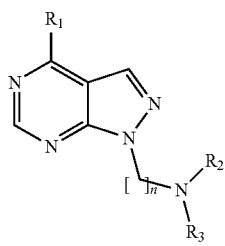

(I)

wherein n is 1, 2, 3 or 4;

$R_1$ represents a carbon-linked substituted or unsubstituted aryl or heteroaryl radical;

$R_2$ and $R_3$ independently represent a hydrogen atom; a branched or unbranched, saturated or unsaturated, optionally at least mono-substituted, aliphatic radical $C_{1-10}$; a substituted or unsubstituted cycloalkyl radical $C_{3-9}$; a branched or unbranched cycloalkyl-alkyl radical $C_{1-10}$ group in which either the alkyl group and/or the cycloalkyl group is optionally at least mono-substituted; a substituted or unsubstituted cycloalkyl $C_{3-9}$ or cycloalkylalkyl $C_{1-10}$ group in which the cycloalkyl group is condensed with another substituted or unsubstituted mono- or polycyclic ring system; a substituted or unsubstituted aryl radical; a substituted or unsubstituted, branched or unbranched arylalkyl radical $C_{1-10}$; a substituted or unsubstituted heteroaryl radical; a substituted or unsubstituted, branched or unbranched heteroarylalkyl radical $C_{1-10}$; a substituted or unsubstituted non-aromatic heterocyclyl radical $C_{3-9}$; a substituted or unsubstituted, branched or unbranched heterocyclylalkyl radical $C_{3-9}$; a substituted or unsubstituted heterocyclyl $C_{3-9}$ or heterocyclyl-alkyl radical $C_{1-10}$ group in which the heterocyclyl group is condensed with another substituted or unsubstituted mono- or polycyclic ring system;

or $R_2$ and $R_3$ together with the bridging nitrogen form a substituted or unsubstituted heterocycloalkyl radical $C_{3-9}$; or a substituted or unsubstituted heteroaryl radical $C_{3-9}$;

or a pharmaceutically acceptable salt, stereoisomer, or solvate thereof.

2. The compound according to claim 1, wherein $R_1$ represents a group selected from:

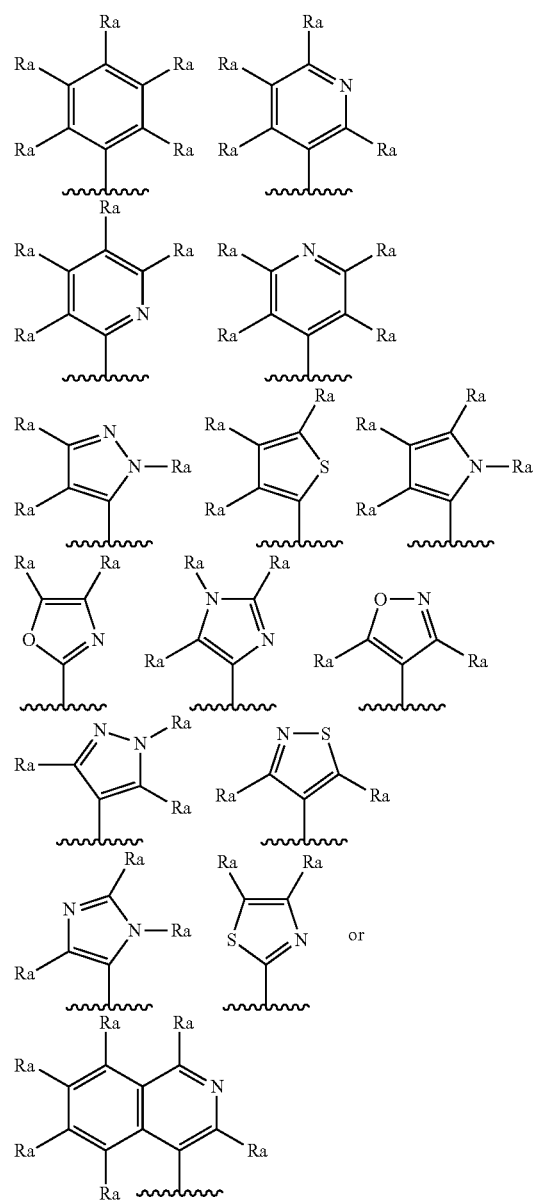

wherein Ra independently represents a hydrogen atom, an alkyl radical $C_1$-$C_6$, a halogen atom, an haloalkyl radical $C_1$-$C_6$, —CN, —OR or —$SO_2R$ where R is hydrogen or an alkyl $C_1$-$C_6$.

3. The compound according to claim 1, wherein $R_2$ and $R_3$ independently represent a branched or unbranched, saturated or unsaturated, optionally at least mono-substituted, aliphatic radical $C_{1-10}$; a substituted or unsubstituted aryl radical; a substituted or unsubstituted, branched or unbranched arylalkyl radical $C_{1-10}$ or an optionally monosubstituted benzhydryl group; or $R_2$ and $R_3$ together with the bridging nitrogen form a substituted or unsubstituted heterocycloalkyl radical $C_{3-9}$; or a substituted or unsubstituted heteroaryl radical $C_{3-9}$.

4. The compound according to claim 3, wherein $R_2$ and $R_3$ together with the bridging nitrogen form a piperidine which is optionally substituted by at least one halogen atom.

5. The compound according to claim 1, wherein n is 2.

6. The compound according to claim 1, which is selected from:
- 4-phenyl-1-(2-(piperidin-1-yl)ethyl)-1H-pyrazolo[3,4-d]pyrimidine,
- 1-(2-(piperidin-1-yl)ethyl)-4-o-tolyl-1H-pyrazolo[3,4-d]pyrimidine,
- 1-(2-(piperidin-1-yl)ethyl)-4-m-tolyl-1H-pyrazolo[3,4-d]pyrimidine hydrochloride,
- 1-(2-(piperidin-1-yl)ethyl)-4-(pyridin-3-yl)-1H-pyrazolo[3,4-d]pyrimidine,
- 4-(2-methylpyridin-3-yl)-1-(2-(piperidin-1-yl)ethyl)-1H-pyrazolo[3,4-d]pyrimidine,
- 3,5-dimethyl-4-(1-(2-(piperidin-1-yl)ethyl)-1H-pyrazolo[3,4-d]pyrimidin-4-yl)isoxazole hydrochloride,
- 4-(4-methoxypyridin-3-yl)-1-(2-(piperidin-1-yl)ethyl)-1H-pyrazolo[3,4-d]pyrimidine hydrochloride,
- 4-(4-methylpyridin-3-yl)-1-(2-(piperidin-1-yl)ethyl)-1H-pyrazolo[3,4-d]pyrimidine hydrochloride,
- 4-(1-methyl-1H-pyrazol-5-yl)-1-(2-(piperidin-1-yl)ethyl)-1H-pyrazolo[3,4-d]pyrimidine,
- 4-(2-methoxypyridin-3-yl)-1-(2-(piperidin-1-yl)ethyl)-1H-pyrazolo[3,4-d]pyrimidine,
- 4-(2-methoxypyridin-3-yl)-1-(2-(piperidin-1-yl)ethyl)-1H-pyrazolo[3,4-d]pyrimidine (L)-tartrate,
- 4-(1-(2-(piperidin-1-yl)ethyl)-1H-pyrazolo[3,4-d]pyrimidin-4-yl)isoquinoline,
- 4-(2-ethoxyphenyl)-1-(2-(piperidin-1-yl)ethyl)-1H-pyrazolo[3,4-d]pyrimidine hydrochloride,
- 4-(4-fluorophenyl)-1-(2-(piperidin-1-yl)ethyl)-1H-pyrazolo[3,4-d]pyrimidine,
- 4-(4-methoxyphenyl)-1-(2-(piperidin-1-yl)ethyl)-1H-pyrazolo[3,4-d]pyrimidine,
- 4-(1-methyl-3-(trifluoromethyl)-1H-pyrazol-5-yl)-1-(2-(piperidin-1-yl)ethyl)-1H-pyrazolo[3,4-d]pyrimidine,
- 4-(1-(2-(piperidin-1-yl)ethyl)-1H-pyrazolo[3,4-d]pyrimidin-4-yl)benzonitrile,
- 4-(5-methylpyridin-3-yl)-1-(2-(piperidin-1-yl)ethyl)-1H-pyrazolo[3,4-d]pyrimidine,
- 1-(2-(piperidin-1-yl)ethyl)-4-(pyridin-2-yl)-1H-pyrazolo[3,4-d]pyrimidine,
- 4-(5-chlorothiophen-2-yl)-1-(2-(piperidin-1-yl)ethyl)-1H-pyrazolo[3,4-d]pyrimidine,
- 4-(4-chlorophenyl)-1-(2-(piperidin-1-yl)ethyl)-1H-pyrazolo[3,4-d]pyrimidine,
- 4-(6-methylpyridin-2-yl)-1-(2-(piperidin-1-yl)ethyl)-1H-pyrazolo[3,4-d]pyrimidine,
- 4-(4-(methylsulfonyl)phenyl)-1-(2-(piperidin-1-yl)ethyl)-1H-pyrazolo[3,4-d]pyrimidine,
- 1-(2-(piperidin-1-yl)ethyl)-4-(1H-pyrazol-4-yl)-1H-pyrazolo[3,4-d]pyrimidine,
- 4-(2-chloro-5-methylphenyl)-1-(2-(piperidin-1-yl)ethyl)-1H-pyrazolo[3,4-d]pyrimidine,
- 4-(2,5-dimethylphenyl)-1-(2-(piperidin-1-yl)ethyl)-1H-pyrazolo[3,4-d]pyrimidine,
- 4-(1-methyl-1H-pyrrol-2-yl)-1-(2-(piperidin-1-yl)ethyl)-1H-pyrazolo[3,4-d]pyrimidine,
- 4-(4-fluoro-2-methoxyphenyl)-1-(2-(piperidin-1-yl)ethyl)-1H-pyrazolo[3,4-d]pyrimidine,
- 4-(4-fluoro-2-methylphenyl)-1-(2-(piperidin-1-yl)ethyl)-1H-pyrazolo[3,4-d]pyrimidine,
- 4-(1-methyl-1H-imidazol-4-yl)-1-(2-(piperidin-1-yl)ethyl)-1H-pyrazolo[3,4-d]pyrimidine,
- 4-(1-methyl-1H-pyrazol-4-yl)-1-(2-(piperidin-1-yl)ethyl)-1H-pyrazolo[3,4-d]pyrimidine,
- 2-(1-(2-(piperidin-1-yl)ethyl)-1H-pyrazolo[3,4-d]pyrimidin-4-yl)oxazole,
- 2-(1-(2-(piperidin-1-yl)ethyl)-1H-pyrazolo[3,4-d]pyrimidin-4-yl)thiazole,
- 4-(4-fluoro-2-(trifluoromethyl)phenyl)-1-(2-(piperidin-1-yl)ethyl)-1H-pyrazolo[3,4-d]pyrimidine,
- 4-(2-chlorophenyl)-1-(2-(piperidin-1-yl)ethyl)-1H-pyrazolo[3,4-d]pyrimidine,
- 4-(1-(2-(piperidin-1-yl)ethyl)-1H-pyrazolo[3,4-d]pyrimidin-4-yl)isothiazole,
- 4-(1-isopropyl-1H-pyrazol-4-yl)-1-(2-(piperidin-1-yl)ethyl)-1H-pyrazolo[3,4-d]pyrimidine,
- 1-(2-(piperidin-1-yl)ethyl)-4-(2-(trifluoromethyl)phenyl)-1H-pyrazolo[3,4-d]pyrimidine,
- 4-(2,4-difluorophenyl)-1-(2-(piperidin-1-yl)ethyl)-1H-pyrazolo[3,4-d]pyrimidine,
- 1-(2-(piperidin-1-yl)ethyl)-4-(pyridin-4-yl)-1H-pyrazolo[3,4-d]pyrimidine,
- 4-(1-methyl-1H-imidazol-5-yl)-1-(2-(piperidin-1-yl)ethyl)-1H-pyrazolo[3,4-d]pyrimidine,
- 4-(2-chloro-4-fluorophenyl)-1-(2-(piperidin-1-yl)ethyl)-1H-pyrazolo[3,4-d]pyrimidine,
- 4-(2-chlorophenyl)-1-(2-(4,4-difluoropiperidin-1-yl)ethyl)-1H-pyrazolo[3,4-d]pyrimidine,
- 4-(2-chloro-4-fluorophenyl)-1-(2-(4,4-difluoropiperidin-1-yl)ethyl)-1H-pyrazolo[3,4-d]pyrimidine,
- 4-(4-chloro-2-fluorophenyl)-1-(2-(4,4-difluoropiperidin-1-yl)ethyl)-1H-pyrazolo[3,4-d]pyrimidine,
- 4-(4-chloro-2-fluorophenyl)-1-(2-(piperidin-1-yl)ethyl)-1H-pyrazolo[3,4-d]pyrimidine,
- 2-(4-(2-chlorophenyl)-1H-pyrazolo[3,4-d]pyrimidin-1-yl)-N-(4-fluorobenzyl)-N-methylethanamine,
- N-(4-fluorobenzyl)-N-methyl-2-(4-(1-methyl-1H-pyrazol-5-yl)-1H-pyrazolo[3,4-d]pyrimidin-1-yl)ethanamine, or
- 2-(4-(2-chloro-4-fluorophenyl)-1H-pyrazolo[3,4-d]pyrimidin-1-yl)-N-(4-fluorobenzyl)-N-methylethanamine, or a pharmaceutically acceptable salt or solvate thereof.

7. A method of treating a condition selected from the group consisting of pain, diarrhea, addiction to cocaine, stroke, depression, anxiety, and schizophrenia in a subject in need thereof comprising administration of an effective amount of the compound according to claim 1.

8. The method according to claim 7, wherein the condition is pain which is selected from the group consisting of neuropathic pain, inflammatory pain, allodynia, and hyperalgesia.

9. The method according to claim 8, wherein the allodynia is mechanical allodynia or thermal allodynia.

10. The method according to claim 8, wherein the neurophatic pain is hyperpathia.

11. The method according to claim 7, wherein the condition is selected from the group consisting of diarrhea, addiction to cocaine, stroke, depression, anxiety, and schizophrenia.

12. A process for the preparation of a compound of general formula (I):

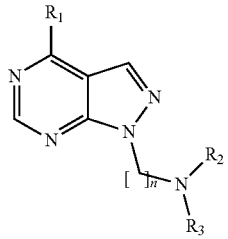

(I)

comprising the reaction between a compound of general formula (III):

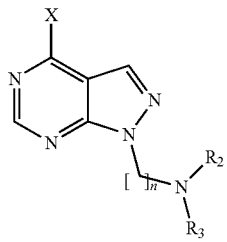

(III)

with a boronic acid of formula (V):

$R_1B(OH)_2$     (V)

a corresponding ester or a corresponding organoborane thereof,
or with an organotin derivative of formula (VI):

$R_1Sn(R_4)_3$ wherein
n is 1, 2, 3 or 4;
$R_1$ represents a carbon-linked substituted or unsubstituted aryl or heteroaryl radical;
$R_2$ and $R_3$ independently represent a hydrogen atom;
a branched or unbranched, saturated or unsaturated, optionally at least mono-substituted, aliphatic radical $C_{1-10}$;
a substituted or unsubstituted cycloalkyl radical $C_{3-9}$; a branched or unbranched cycloalkyl-alkyl radical $C_{1-10}$ group in which either the alkyl group and/or the cycloalkyl group is optionally at least mono-substituted; a substituted or unsubstituted cycloalkyl $C_{3-9}$ or cycloalkylalkyl $C_{1-10}$ group in which the cycloalkyl group is condensed with another substituted or unsubstituted mono- or polycyclic ring system;
a substituted or unsubstituted aryl radical; a substituted or unsubstituted, branched or unbranched arylalkyl radical $C_{1-10}$;
a substituted or unsubstituted heteroaryl radical; a substituted or unsubstituted, branched or unbranched heteroarylalkyl radical $C_{1-10}$; a substituted or unsubstituted non-aromatic heterocyclyl radical $C_{3-9}$; a substituted or unsubstituted, branched or unbranched heterocyclylalkyl radical $C_{3-9}$;
a substituted or unsubstituted heterocyclyl $C_{3-9}$ or heterocyclyl-alkyl radical $C_{1-10}$ group in which the heterocyclyl group is condensed with another substituted or unsubstituted mono- or polycyclic ring system;

or $R_2$ and $R_3$ together with the bridging nitrogen form a substituted or unsubstituted heterocycloalkyl radical $C_{3-9}$; or a substituted or unsubstituted heteroaryl radical $C_{3-9}$;
X is a halogen atom; and
$R_4$ represents a $C_1$-$C_{10}$ alkyl radical.

13. The process according to claim 12, wherein the compound of formula (III):

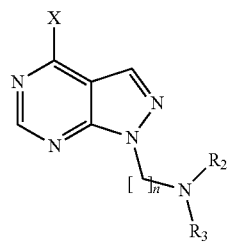

(III)

is prepared by a reaction between a compound of general formula (II):

(II)

with a compound of formula general (IV):

(IV)

wherein
n is 1, 2, 3 or 4;
$R_2$ and $R_3$ independently represent a hydrogen atom;
a branched or unbranched, saturated or unsaturated, optionally at least mono-substituted, aliphatic radical $C_{1-10}$;
a substituted or unsubstituted cycloalkyl radical $C_{3-9}$; a branched or unbranched cycloalkyl-alkyl radical $C_{1-10}$ group in which either the alkyl group and/or the cycloalkyl group is optionally at least mono-substituted; a substituted or unsubstituted cycloalkyl $C_{3-9}$ or cycloalkylalkyl $C_{1-10}$ group in which the cycloalkyl group is condensed with another substituted or unsubstituted mono- or polycyclic ring system;
a substituted or unsubstituted aryl radical; a substituted or unsubstituted, branched or unbranched arylalkyl radical $C_{1-10}$;
a substituted or unsubstituted heteroaryl radical; a substituted or unsubstituted, branched or unbranched heteroarylalkyl radical $C_{1-10}$; a substituted or unsubstituted non-aromatic heterocyclyl radical $C_{3-9}$; a substituted or unsubstituted, branched or unbranched heterocyclylalkyl radical $C_{3-9}$;
a substituted or unsubstituted heterocyclyl $C_{3-9}$ or heterocyclyl-alkyl radical $C_{1-10}$ group in which the heterocyclyl group is condensed with another substituted or unsubstituted mono- or polycyclic ring system;

or $R_2$ and $R_3$ together with the bridging nitrogen form a substituted or unsubstituted heterocycloalkyl radical $C_{3-9}$; or a substituted or unsubstituted heteroaryl radical $C_{3-9}$;

X is a halogen atom or triflate; and

Y is a suitable leaving group, including a halogen atom or a hydroxyl group.

14. A pharmaceutical composition comprising the compound according to claim 1, and at least a pharmaceutically acceptable carrier, additive, adjuvant or vehicle.

* * * * *